United States Patent
Shu et al.

(10) Patent No.: US 12,290,541 B2
(45) Date of Patent: May 6, 2025

(54) **STRAIN OF *LACTOBACILLUS HELVETICUS* CAPABLE OF REMOVING MULTIPLE HEAVY METALS AND APPLICATION THEREOF IN GOAT MILK POWDER**

(71) Applicant: SHAANXI UNIVERSITY OF SCIENCE AND TECHNOLOGY, Xi'an (CN)

(72) Inventors: Guowei Shu, Xi'an (CN); Ke Zhang, Xi'an (CN); Huan Lei, Xi'an (CN); Qisheng Hu, Xi'an (CN); Guanli Du, Xi'an (CN); Qiqi Zheng, Xi'an (CN); Guoliang Li, Xi'an (CN); Qinfeng Xu, Xi'an (CN); Chunji Dai, Xi'an (CN); Ting Li, Xi'an (CN); Wenjing Hu, Xi'an (CN); Lihao Xu, Xi'an (CN); Chaowei Yang, Xi'an (CN); Jie Qiao, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 18/809,763

(22) Filed: Aug. 20, 2024

(65) Prior Publication Data
US 2025/0064872 A1   Feb. 27, 2025

(30) Foreign Application Priority Data
Aug. 25, 2023   (CN) .......................... 202311082650.0

(51) Int. Cl.
| | | |
|---|---|---|
| A61K 35/747 | (2015.01) | |
| A61K 35/00 | (2006.01) | |
| A61K 35/20 | (2006.01) | |
| A61P 39/04 | (2006.01) | |

(52) U.S. Cl.
CPC ............ *A61K 35/747* (2013.01); *A61K 35/20* (2013.01); *A61P 39/04* (2018.01); *A61K 2035/115* (2013.01)

(58) Field of Classification Search
None
See application file for complete search history.

(56) References Cited

FOREIGN PATENT DOCUMENTS

| | | |
|---|---|---|
| CN | 109517763 | 3/2019 |
| CN | 116590186 | 8/2023 |
| CN | 117070414 | 11/2023 |

OTHER PUBLICATIONS

Xu et al. Fermentation 10: 1-15, Jan. 4, 2024.*
GenEmbl accession # HM218413, pp. 1-3, Sep. 20, 2010.*
Shu et al. LWT—Food Sci. Technol. 90: 70-76, 2018.*
Notification to Grant Patent Right for Invention for Chinese Patent Application No. 202311082650.0, issued Jan. 31, 2024, 4 pages.
Notice of the First Office Action for Chinese Patent Application No. 202311082650.0, issued Jan. 10, 2024, 7 pages.
First Search Report for Chinese Patent Application No. 202311082650.0, issued Jan. 8, 2024, 4 pages.
Supplemental Search Report for Chinese Patent Application No. 202311082650.0, issued Jan. 26, 2024, 4 pages.
Masood, et al., "Single and multi-component adsorption of metal ions by *Acinetobacter* sp. FM4," Separation Science and Technology 50.6, Nov. 2015, pp. 892-900.
Ziagova, et al., "Comparative study of Cd (II) and Cr (VI) biosorption on *Staphylococcus xylosus* and *Pseudomonas* sp. in single and binary mixtures," Bioresource Technology 98.15, 2007, pp. 2859-2865.
Sati, et al., "Biosorption of heavy metals from single and multimetal solutions by free and immobilized cells of Bacillus megaterium," Int. J. Adv. Res 2, 2014, pp. 923-934.
Parungao, et al., "Biosorption of copper, cadmium and lead by copper-resistant bacteria isolated from Mogpog River, Marinduque," Philippine journal of science 136.2, 2007, pp. 155-165.
Wang, et al., "Biosorption of heavy metals from aqueous solution by UV-mutant Bacillus subtilis," Environmental Science and Pollution Research 20, 2013, pp. 7450-7463.

* cited by examiner

*Primary Examiner* — S. Devi
(74) *Attorney, Agent, or Firm* — DLA PIPER LLP (US)

(57) ABSTRACT

Disclosed are a strain of *Lactobacillus helveticus* capable of removing multiple heavy metals and an application thereof in milk powder, where the strain is *Lactobacillus helveticus* KD-3, which is deposited in the China Center for Type Culture Collection on Apr. 6, 2023, with a deposit number of CCTCC NO: M2023479. The *Lactobacillus helveticus* KD-3 has a cadmium resistant gene czcD, a chromium resistant gene chrA and a lead resistant gene pbrT, and is capable of tolerating single and compound heavy metals (cadmium, chromium and lead). The *Lactobacillus helveticus* KD-3 of the present disclosure is used to prepare lyophilized bacterial powder.

2 Claims, 24 Drawing Sheets
Specification includes a Sequence Listing.

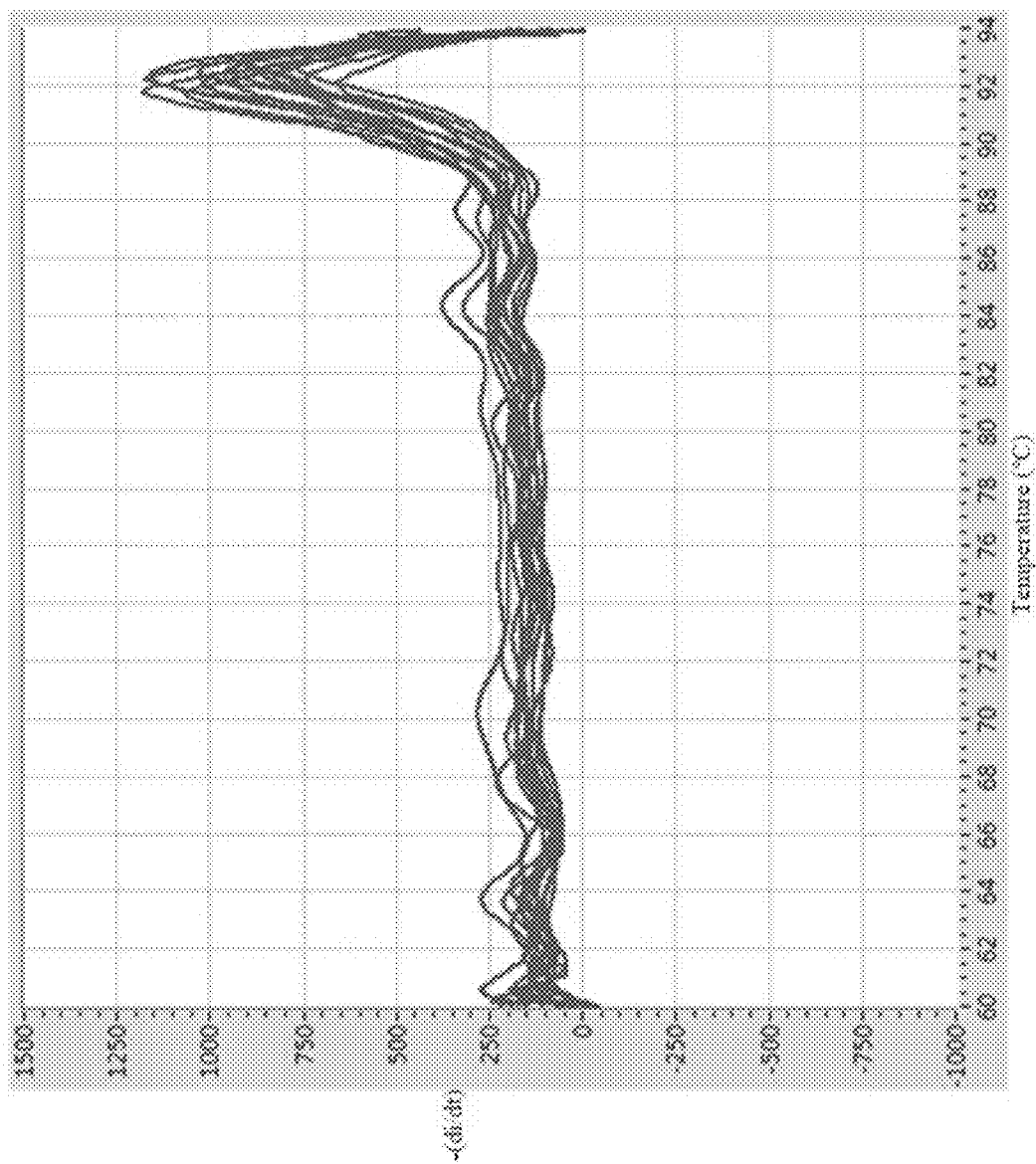

SEQUENCE LISTING

```
Sequence total quantity: 7
SEQ ID NO: 1            moltype = DNA   length = 1478
FEATURE                 Location/Qualifiers
source                  1..1478
                        mol_type = other DNA
                        organism = synthetic construct
SEQUENCE: 1
acgctggcgg cgtgcctaat acatgcaagt cgagcgagca gaaccagcag atttacttcg   60
gtaatgacgc tggggacgcg agcggcggat gggtgagtaa cacgtgggga acctgcccca  120
tagtctagga taccacttgg aaacaggtgc taataccgga taataaagca gatcgcatga  180
tcagcttata aaaggcggcg taagctgtcg ctatggatg gccccgcggt gcattagcta   240
gttggtaagg taacggctta ccaaggcaat gatgcatagc cgagttgaga gactgaacgg  300
ccacattggg actgagacac ggcccaaact cctacgggag gcagcagtag ggaatcttcc  360
acaatggacg caagtctgat ggagcaacgc cgcgtgagtg aagaaggttt tcggatcgta  420
aagctctgtt gttggtgaag aaggatagag gtagtaactg cctttatt gacggtaatc   480
aaccagaaag tcacggctaa ctacgtgcca gcagccgcgg taatacgtag gtggcaagcg  540
ttgtccggat ttattgggcg taaagcgagc gcaggcggaa gaataagtct gatgtgaaag  600
ccctcggctt aaccgaggaa ttgcatcgga aactgttttt cttgagtgca gaagaggaga  660
gtggaactcc atgtgtagcg gtggaatgcg tagatatatg gaagaacacc agtggcgaag  720
gcggctctct ggtctgcaac tgacgctgag gctcgaaagc atgggtagcg aacaggatta  780
gataccctgg tagtccatgc cgtaaacgat gagtgctaag tgttgggagg tttccgcctc  840
tcagtgctgc agctaacgca ttaagcactc cgcctgggga gtacgaccgc aaggttgaaa  900
ctcaaaggaa ttgacggggg cccgcacaag cggtggagca tgtggtttaa ttcgaagcaa  960
cgcgaagaac cttaccaggt cttgacatct agtgccatcc taagagatta ggagttccct 1020
tcggggacgc taagacaggt ggtgcatggc tgtcgtcagc tcgtgtcgtg agatgttggg 1080
ttaagtcccg caacgagcgc aacccttatt attagttgcc agcattaagt tgggcactct 1140
aatgagactg ccggtgacaa accggaggaa ggtggggatg acgtcaagtc atcatgcccc 1200
ttatgacctg ggctacacac gtgctacaat gggcagtaca acgagaagcg agcctgcgaa 1260
ggcaagcgaa tctctgaaag ctgttctcag ttcggactgc agtctgcaac tcgactgcac 1320
gaagctggaa tcgctagtaa tcgcggatca gaacgccgcg gtgaatacgt tcccgggcct 1380
tgtacacacc gcccgtcaca ccatggaagt ctgcaatgcc caaagccggt ggcctaacct 1440
tcgggaagga gccgtctaag gcagggcaga tgactggg                         1478

SEQ ID NO: 2            moltype = DNA   length = 25
FEATURE                 Location/Qualifiers
source                  1..25
                        mol_type = other DNA
                        organism = synthetic construct
SEQUENCE: 2
agcgcgccca ggagcgcagc gtctt                                         25

SEQ ID NO: 3            moltype = DNA   length = 20
FEATURE                 Location/Qualifiers
source                  1..20
                        mol_type = other DNA
                        organism = synthetic construct
misc_difference         18
                        note = a or g
SEQUENCE: 3
ggctcgaagc cgtcgagrta                                               20

SEQ ID NO: 4            moltype = DNA   length = 20
FEATURE                 Location/Qualifiers
source                  1..20
                        mol_type = other DNA
                        organism = synthetic construct
SEQUENCE: 4
tggctctcgc tgttctttgt                                               20

SEQ ID NO: 5            moltype = DNA   length = 20
FEATURE                 Location/Qualifiers
source                  1..20
                        mol_type = other DNA
                        organism = synthetic construct
SEQUENCE: 5
taagtgcgac aagggcaact                                               20

SEQ ID NO: 6            moltype = DNA   length = 22
FEATURE                 Location/Qualifiers
source                  1..22
                        mol_type = other DNA
                        organism = synthetic construct
SEQUENCE: 6
tcatcgccgg tgcgatcatc at                                            22

SEQ ID NO: 7            moltype = DNA   length = 20
FEATURE                 Location/Qualifiers
source                  1..20
```

```
                 mol_type = other DNA
                 organism = synthetic construct
SEQUENCE: 7
tgtcattcac gacatgaacc                                             20
```

STRAIN OF *LACTOBACILLUS HELVETICUS* CAPABLE OF REMOVING MULTIPLE HEAVY METALS AND APPLICATION THEREOF IN GOAT MILK POWDER

CROSS-REFERENCE TO RELATED APPLICATIONS

This application claims priority to Chinese Patent Application No. 202311082650.0, filed on Aug. 25, 2023, the contents of which are hereby incorporated by reference.

INCORPORATION BY REFERENCE STATEMENT

The Sequence Listing XML associated with this application is provided electronically in XML file format and is hereby incorporated by reference into the specification. The name of the XML file containing the Sequence Listing is "PPH-US 2024-9131Sequence-V1.xml". The XML file is 9,229 bytes, created on Aug. 21, 2024, and is being submitted electronically via USPTO Patent Center.

TECHNICAL FIELD

The present disclosure belongs to the field of microbial technology and specifically relates to a strain of *Lactobacillus helveticus* capable of removing multiple heavy metals and an application thereof in goat milk powder.

BACKGROUND

Heavy metals are considered to be one of the most polluting substances globally, which may enter the human body through the food chain and pose health risks to humans. Methods for processing heavy metal pollution are diverse. However, simple physicochemical methods fail to efficiently remove lead, cadmium, chromium and other heavy metal ions from the environment, while microbial treatment has obvious advantages such as high treatment capacity, adaptability to the environment, low cost and environmental friendliness.

To date, several microbial agents (bacteria, fungi, and microalgae) have been identified as biological scavenging methods. Lactic acid bacteria play an important role as food-safe grade microorganisms in the human gut, and heavy metal removal techniques based on lactic acid bacteria are increasingly emphasized by researchers. In the prior art, *Lactobacillus* may effectively remove heavy metals from foodstuffs by surface adsorption and in vivo accumulation. Studies have focused on the screening of lactic acid bacteria for the removal of single heavy metals, such as *L. plantarum* CICC21805 with 85.73% removal efficiency of cadmium in rice, *L. plantarum* CCFM8610 with 31.34% removal efficiency of cadmium in aqueous solution, *E. faecium* EF031 with 66.9% removal efficiency of lead in aqueous solution, *E. faecium* JT1 with 66.95% removal efficiency of lead in mouse gastric solution, and *L. plantarum* TW1-1 with efficacy in removing chromium from gastrointestinal fluids of mice. However, the contamination in the environment and food often involves the contamination of multiple heavy metals, so it is necessary to screen lactic acid bacteria that are capable of tolerating and removing multiple heavy metals at the same time.

SUMMARY

The objective of the present disclosure is to provide a strain of *Lactobacillus helveticus* capable of removing multiple heavy metals and an application thereof in goat milk powder, where the *Lactobacillus helveticus* KD-3 is tolerant to single and compound heavy metals (cadmium, chromium and lead) and has a high removal efficiency for single and compound heavy metals (cadmium, chromium and lead).

The present disclosure provides a strain of *Lactobacillus helveticus* KD-3 capable of removing multiple heavy metals, and the strain is deposited in the China Center for Type Culture Collection on Apr. 6, 2023, with a deposit number of CCTCC NO: M2023479.

Optionally, a medium applied in a culture of the *Lactobacillus helveticus* KD-3 includes an MRS (deMan, Rogosa, Sharpe) broth liquid medium, where a pH value of the culture is 5-8, a temperature of the culture is 37-40 degrees Celsius (° C.), and an inoculum amount for the culture is 2%-5% of a volume of the MRS broth liquid medium; and the *Lactobacillus helveticus* KD-3 is capable of tolerating a NaCl solution with a mass concentration of 2%.

The present disclosure provides an application of the *Lactobacillus helveticus* KD-3 according to the above technical scheme for removing heavy metals of cadmium, chromium and lead.

Optionally, the application includes: inoculating the *Lactobacillus helveticus* KD-3 into an MRS broth liquid medium containing cadmium, chromium and lead for culture to remove the heavy metals cadmium, chromium and lead from the MRS broth liquid medium; where an inoculation amount of the *Lactobacillus helveticus* KD-3 in the culture is 2%-5% of a volume of the MRS broth liquid medium, and a temperature of the culture is 37-40° C., a pH is 5-8, and a culture duration is 24 hours (h);

or:

mixing cells of the *Lactobacillus helveticus* KD-3 directly with a solution containing cadmium and lead or chromium alone for adsorption;

where a preparation of the cells of the *Lactobacillus helveticus* KD-3 includes: obtaining a culture solution by culturing the *Lactobacillus helveticus* KD-3 in accordance with culture conditions described in the above technical scheme, centrifuging the culture solution at 4° C. to obtain the cells, and washing the cells using sterile saline for 2 times to obtain the cells.

Optionally, a concentration of $Pb^{2+}$ in the MRS broth liquid medium is ≤1500 milligrams per liter (mg/L), a concentration of $Cd^{2+}$ in the MRS broth liquid medium is ≤150 mg/L, and a concentration of $Cr^{6+}$ in the MRS broth liquid medium is ≤1500 mg/L;

when contents of the heavy metals of cadmium, chromium and lead in the MRS broth liquid medium are all 60 mg/L, a removal rate of the cadmium by the *Lactobacillus helveticus* KD-3 is 37.54±0.85%, and an adsorption amount is 159 milligrams per gram (mg/g); a removal rate of the chromium by the *Lactobacillus helveticus* KD-3 is 60.44±1.28%, and an adsorption amount is 207 mg/g; a removal rate of the lead by the *Lactobacillus helveticus* KD-3 is 34.01±0.12%, with an adsorption amount of 142 mg/g.

Optionally, when an addition amount of the bacteria of the *Lactobacillus helveticus* KD-3 is 5-7% of a volume of the solution containing cadmium and lead, a pH of the solution is 6.5-7.5, an adsorption temperature is 35-45° C. and an adsorption duration is 1.5-3.5 h, a removal rate of the cadmium in the solution containing cadmium and lead is 36.50%-65.67% and a removal rate of the lead is 72.45%-94.17%;

when an addition amount of the bacteria of the *Lactobacillus helveticus* KD-3 is 2-10% of the solution containing chromium alone, a pH of the solution is 2-4, an adsorption temperature is 32-37° C. and an adsorption duration is 3-4 h, a removal rate of the cadmium is 24.08%-57.16%.

The present disclosure provides an application of the *Lactobacillus helveticus* KD-3 according to the above technical scheme in preparing products with antioxidant properties or in increasing lactic acid yield.

The present disclosure provides a scavenger for removing heavy metal contamination, including viable bacteria, dead bacteria or lyophilized powder added with protective agents of *Lactobacillus helveticus* KD-3 according to the above technical scheme.

The present disclosure provides a functional probiotic goat milk powder for removing heavy metals, where the functional probiotic goat milk powder includes a lyophilized powder prepared from the *Lactobacillus helveticus* KD-3 according to the above technical scheme.

Optionally, an effective viable bacterial count of the *Lactobacillus helveticus* KD-3 in the functional probiotic goat milk powder is ≥3.0×10$^7$ colony forming units per gram (CFU/g).

Beneficial effect of the present disclosure: the present disclosure provides a strain of *Lactobacillus helveticus* KD-3 capable of removing multiple heavy metals, which is deposited in the China Center for Type Culture Collection on Apr. 6, 2023, with the deposit number of CCTCC NO: M2023479. The *Lactobacillus helveticus* KD-3 has the cadmium resistant gene czcD, chromium resistant gene chrA and lead resistant gene pbrT, with tolerance against single and compound heavy metals (cadmium, chromium and lead), and the removal efficiency for single and compound heavy metals (cadmium, chromium and lead) is high. The *Lactobacillus helveticus* KD-3 provided by the present disclosure may be used to prepare lyophilized cells powder, which is used to develop a goat milk powder containing the *Lactobacillus helveticus* KD-3, and the prepared lyophilized powder and the goat milk powder are both effective in removing heavy metals.

BRIEF DESCRIPTION OF THE DRAWINGS

In order to more clearly illustrate the technical schemes in the embodiments or prior art of the present disclosure, the accompanying drawings to be used in the embodiments are briefly described below. Note: different letter labels in FIG. 1, FIG. 3, FIG. 4 to FIG. 6, and FIG. 9 to FIG. represent significant differences between groups, p<0.05.

FIG. 8F shows the lysis curves of the resistant genes pbrT.

Figure 1:
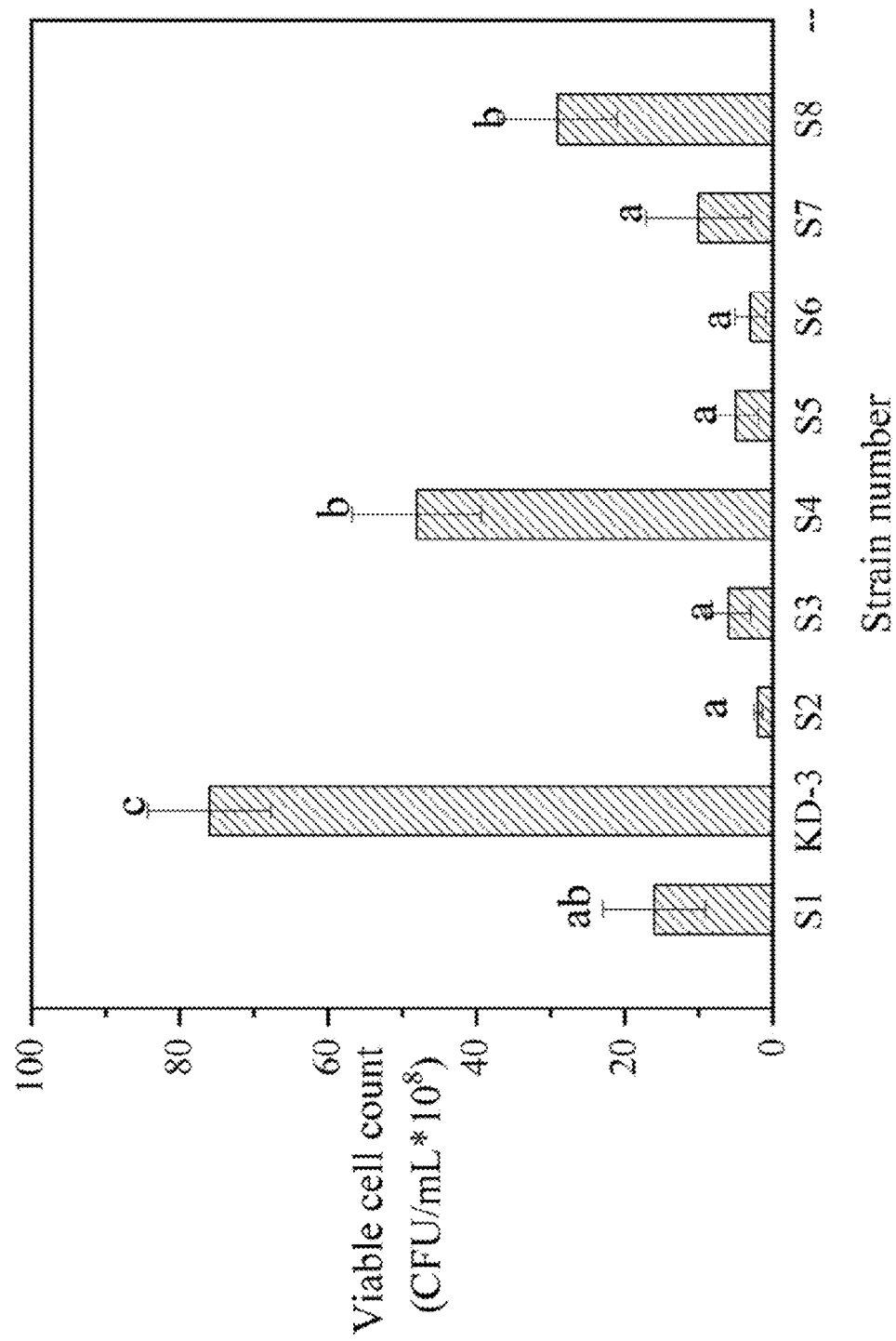
FIG. 1 shows the results of the screening of lead-resistant lactic acid bacteria.

Bio-Depository Certificate:

*Lactobacillus helveticus* KD-3, deposited in the China Center for Type Culture Collection (CCTCC) on Apr. 6, 2023, with the deposit number CCTCC NO: M2023479, the address of the depository unit is No. 299, Bayi Road, Wuchang District, Wuhan City, Hubei Province, China.

DETAILED DESCRIPTION OF THE EMBODIMENTS

The present disclosure provides a strain of *Lactobacillus helveticus* KD-3 capable of removing multiple heavy metals, with the deposit number CCTCC NO: M2023479. The 16S rDNA gene sequence of the *Lactobacillus helveticus* KD-3 described herein is as shown in SEQ ID NO. 1.

SEQ ID NO. 1 sequence:
ACGCTGGCGGCGTGCCTAATACATGCAAGTCGAGCGAGCAGAACCAGCA

GATTTACTTCGGTAATGACGCTGGGGACGCGAGCGGCGGATGGGTGAGT

AACACGTGGGGAACCTGCCCCATAGTCTAGGATACCACTTGGAAACAGG

TGCTAATACCGGATAATAAAGCAGATCGCATGATCAGCTTATAAAAGGC

GGCGTAAGCTGTCGCTATGGGATGGCCCCGCGGTGCATTAGCTAGTTGG

TAAGGTAACGGCTTACCAAGGCAATGATGCATAGCCGAGTTGAGAGACT

GAACGGCCACATTGGGACTGAGACACGGCCCAAACTCCTACGGGAGGCA

GCAGTAGGGAATCTTCCACAATGGACGCAAGTCTGATGGAGCAACGCCG

-continued

```
CGTGAGTGAAGAAGGTTTTCGGATCGTAAAGCTCTGTTGTTGGTGAAGA

AGGATAGAGGTAGTAACTGGCCTTTATTTGACGGTAATCAACCAGAAAG

TCACGGCTAACTACGTGCCAGCAGCCGCGGTAATACGTAGGTGGCAAGC

GTTGTCCGGATTTATTGGGCGTAAAGCGAGCGCAGGCGGAAGAATAAGT

CTGATGTGAAAGCCCTCGGCTTAACCGAGGAATTGCATCGGAAACTGTT

TTTCTTGAGTGCAGAAGAGGAGAGTGGAACTCCATGTGTAGCGGTGGAA

TGCGTAGATATATGGAAGAACACCAGTGGCGAAGGCGGCTCTCTGGTCT

GCAACTGACGCTGAGGCTCGAAAGCATGGGTAGCGAACAGGATTAGATA

CCCTGGTAGTCCATGCCGTAAACGATGAGTGCTAAGTGTTGGGAGGTTT

CCGCCTCTCAGTGCTGCAGCTAACGCATTAAGCACTCCGCCTGGGGAGT

ACGACCGCAAGGTTGAAACTCAAAGGAATTGACGGGGGCCCGCACAAGC

GGTGGAGCATGTGGTTTAATTCGAAGCAACGCGAAGAACCTTACCAGGT

CTTGACATCTAGTGCCATCCTAAGAGATTAGGAGTTCCCTTCGGGACG

CTAAGACAGGTGGTGCATGGCTGTCGTCAGCTCGTGTCGTGAGATGTTG

GGTTAAGTCCCGCAACGAGCGCAACCCTTATTATTAGTTGCCAGCATTA

AGTTGGGCACTCTAATGAGACTGCCGGTGACAAACCGGAGGAAGGTGGG

GATGACGTCAAGTCATCATGCCCCTTATGACCTGGGCTACACACGTGCT

ACAATGGGCAGTACAACGAGAAGCGAGCCTGCGAAGGCAAGCGAATCTC

TGAAAGCTGTTCTCAGTTCGGACTGCAGTCTGCAACTCGACTGCACGAA

GCTGGAATCGCTAGTAATCGCGGATCAGAACGCCGCGGTGAATACGTTC

CCGGGCCTTGTACACACCGCCCGTCACACCATGGAAGTCTGCAATGCCC

AAAGCCGGTGGCCTAACCTTCGGGAAGGAGCCGTCTAAGGCAGGGCAGA

TGACTGGG.
```

The *Lactobacillus helveticus* KD-3 described in the present disclosure is screened from milk Kefir grains, and the colonies are milky-white with convex and relatively smooth appearance, and the cellular morphology is in line with the typical morphological characteristics of lactic acid bacteria. Scanning electron microscopy results show that the surface of the cells is smooth and free of foreign matter, and the cells is rod-shaped and full. Microscopic observation shows rod shape.

The present disclosure compares the 16S rDNA sequence of the strain KD-3 with the data in the NCBI database to preliminarily determine the taxonomic information of the strain, and by constructing a phylogenetic tree of strain KD-3, the identification results show that strain KD-3 is a strain of *Lactobacillus helveticus*.

The *Lactobacillus helveticus* KD-3 of the present disclosure has a cadmium resistant gene czcD, a chromium resistant gene chrA, and a lead resistant gene pbrT, and is capable of tolerating single and compound heavy metals (cadmium, chromium, and lead) as well as having a high efficiency of removal of single and compound heavy metals (cadmium, chromium, and lead). The *Lactobacillus helveticus* KD-3 has a high DPPH radical scavenging and high lactic acid production.

In the present disclosure, the medium applied in the culture of the *Lactobacillus helveticus* KD-3 preferably includes MRS broth liquid medium, the pH value of the culture preferably ranges from 5 to 8, more preferably 7, and the temperature of the culture preferably ranges from 37 to 40° C., more preferably 37° C., and the inoculum amount of the culture ranges from 2% to 5% of the volume of the MRS broth liquid medium, more preferably 3%, and the *Lactobacillus helveticus* KD-3 is capable of tolerating the NaCl solution with a mass concentration of 2%.

The present disclosure provides an application of the *Lactobacillus helveticus* KD-3 according to the above technical scheme or the cells according to the above technical scheme for use in the removal of the heavy metals cadmium, chromium and lead. The heavy metals cadmium, chromium and lead described in the present disclosure all refer to compounds containing the heavy metals cadmium, chromium and lead, and do not involve heavy metal monomers.

In the present disclosure, the application preferably includes inoculating the *Lactobacillus helveticus* KD-3 in MRS broth liquid medium containing cadmium, chromium and lead for culture to remove the heavy metals cadmium, chromium and lead from the MRS broth liquid medium; the inoculum amount of the *Lactobacillus helveticus* KD-3 in the culture is in an amount of 2%-5% of the volume of the MRS broth liquid medium, the temperature of the culture is 37-40° C., the pH value is 5-8, and the duration of the culture is 24-48 h;

or:

mixing the cells of the *Lactobacillus helveticus* KD-3 directly with a solution containing cadmium and lead or chromium alone for adsorption;

The preparation of the cells of the *Lactobacillus helveticus* KD-3 of the present disclosure includes: inoculating the *Lactobacillus helveticus* KD-3 in the MRS broth liquid medium for culture to obtain a *Lactobacillus helveticus* KD-3 fermentation broth, centrifuging the *Lactobacillus helveticus* KD-3 fermentation broth to collect the cells, washing the cells with sterile saline for 2 times and centrifuging again to obtain the cells. The number of washing with the saline of the present disclosure is preferably 2 times. The temperature of the culture of the present disclosure is preferably 37-40° C.; the duration of the culture is preferably 24 h. The duration of the centrifuging of the present disclosure is preferably 9-11 minutes (min), more preferably 10 min; the rotational speed of the centrifuging is preferably 7800-8200 revolutions per minute (rpm), more preferably 8000 rpm. The washing of the present disclosure is preferably performed by using the sterile saline to wash for two times.

In the present disclosure, the concentration of $Pb^{2+}$ in the MRS broth liquid medium is preferably ≤1500 mg/L, more preferably 1500 mg/L; the concentration of $Cd^{2+}$ in the MRS broth liquid medium is preferably ≤150 mg/L, more preferably 150 mg/L; and the concentration of $Cr^{6+}$ in the MRS broth liquid medium is preferably ≤1500 mg/L, more preferably 1500 mg/L.

In the embodiments of the present disclosure, when the contents of heavy metals cadmium, chromium and lead in the MRS broth liquid medium are all 60 mg/L, the removal rate of *Lactobacillus helveticus* KD-3 for cadmium is 37.54±0.85%, and the adsorption amount is 159 mg/g; the removal rate of *Lactobacillus helveticus* KD-3 for chromium is 60.44±1.28%, and the adsorption amount is 207 mg/g; the removal rate of *Lactobacillus helveticus* KD-3 for lead is 34.01±0.12% and the adsorption amount is 142 mg/g.

The *Lactobacillus helveticus* KD-3 described in the present disclosure grows well on the MRS broth agar medium with the simultaneous addition of $Pb^{2+}$ concentration 1500 mg/L, $Cd^{2+}$ 150 mg/L, $Cr^{6+}$ 1500 mg/L, with the number of colonies of 10-100, and grow excellently on MRS agar medium with the simultaneous addition of $Pb^{2+}$ concentration 1000 mg/L, $Cd^{2+}$ 100 mg/L, $Cr^{6+}$ 1000 mg/L, with the number of colonies of 10-300.

According to the present disclosure, the *Lactobacillus helveticus* KD-3 cells are directly mixed with solution containing cadmium and lead or solution containing chromium alone for adsorption. The solution containing cadmium and lead of the present disclosure are preferably solution of cadmium-containing compounds and lead-containing compounds formulated directly using the solvent water. The concentration of cadmium in the solution containing cadmium and lead described herein is preferably 100 mg/L, and the concentration of lead is preferably 100 mg/L. The solution containing cadmium and lead of the present disclosure is preferably solution of cadmium-containing compounds and lead-containing compounds formulated directly using the solvent water.

The solution containing chromium alone described in the present disclosure is preferably a solution of the chromium-containing compound formulated directly using the solvent water, and the concentration of chromium in the chromium-containing solution described in the present disclosure is preferably 100 mg/L.

In an embodiment of the present disclosure, when the addition amount of *Lactobacillus helveticus* KD-3 is 5-7% of the volume of the solution containing cadmium and lead, the pH value of the solution is 6.5-7.5, the adsorption temperature is 35-45° C., and the adsorption duration is 1.5-3.5 h, the removal rate of cadmium in the solution containing cadmium and lead is 36.50%-65.67%, and the removal rate of lead in the solution containing cadmium and lead is 72.45%-94.17%; in an embodiment of the present disclosure, when the addition amount of *Lactobacillus helveticus* KD-3 is 2-10% of the volume of the solution containing chromium alone, the pH of the solution is 2-4, the adsorption temperature is 32-37° C. and the adsorption duration is 3-4 h, the removal rate of chromium is 24.08%-57.16%.

When the *Lactobacillus helveticus* KD-3 adsorbs cadmium ions, the adsorption temperature is preferably 40° C. with a maximum cadmium removal rate of 29.08±1.13%; when adsorbing lead ions, the adsorption temperature is preferably 37° C. with a maximum lead ion removal rate of 75.88±2.54%; and as for adsorbing chromium ions, the adsorption temperature is preferably 32° C. with a maximum chromium ion removal rate of 38.85±1.45%.

The adsorption pH value of *Lactobacillus helveticus* KD-3 is preferably 4-7, more preferably 5-6. When adsorbing cadmium ions, the pH value is preferably 7; When lead ions are adsorbed, the pH value is preferably 6; when chromium ions are adsorbed, the pH value is preferably 4.

The adsorption duration of the *Lactobacillus helveticus* KD-3 described in the present disclosure is preferably 1-3 h, more preferably 3 h. When cadmium ions are adsorbed, the adsorption time is preferably 3 h. When lead ions are adsorbed, the adsorption time is preferably 2 h. When chromium ions are adsorbed, the adsorption time is preferably 3 h.

When the *Lactobacillus helveticus* KD-3 cells adsorb cadmium ions, the addition amount of the cells is preferably 6% of the volume of the solution containing cadmium and lead; as for adsorbing lead ions, the addition amount of the cells is preferably 6% of the volume of the solution containing cadmium and lead; and as for adsorbing chromium ions, the addition amount of the cells is preferably 8% of the volume of the solution containing chromium. The maximum values of lead and cadmium ion removal rates are 65.87±1.55% and 28.64±0.48% respectively when the addition amount of the cells is preferably 6% of the volume of the solution containing cadmium and lead; and the maximum value of the removal rate of chromium ions is 46.74±1.52% when the addition amount of the cells is preferably 8% of the volume of the solution containing chromium.

In an embodiment of the present disclosure, the *Lactobacillus helveticus* KD-3 is inoculated in the MRS broth liquid medium according to the inoculum amount of 5% of the volume of MRS broth liquid medium, and the concentrations of cadmium, chromium, and lead in this MRS broth liquid medium are all 60 mg/L; lead, cadmium and chromium in heavy metal solutions are removed by *Lactobacillus helveticus* KD-3, and the concentrations of lead ions, cadmium ions and chromium ions are all 100 mg/L; the concentrations of these heavy metals are much higher than the concentrations of heavy metals in actual samples in nature, indicating that the *Lactobacillus helveticus* KD-3 of the present disclosure has a good adsorption effect on heavy metals.

The present disclosure provides an application of the *Lactobacillus helveticus* KD-3 according to the above technical scheme in preparing products with antioxidant properties or in increasing lactic acid yield.

The present disclosure provides a scavenger for removing heavy metal contamination, including viable cells, dead cells or lyophilized powder of *Lactobacillus helveticus* added with protective agents according to the above technical scheme.

The method of preparing the lyophilized powder of the present disclosure preferably includes: centrifuging and washing the *Lactobacillus helveticus* KD-3 cells to obtain the cells, mixing the cells with a protective agent and then performing vacuum freeze-drying to obtain *Lactobacillus helveticus* KD-3 lyophilized powder. The preparation method of the *Lactobacillus helveticus* KD-3 cells has been discussed above and will not be repeated herein. Optionally, when the protective agent described in the present disclosure is added, the corresponding mass of glucose, D-galactose and ascorbic acid is first dissolved into sterile water to obtain the protective agent solution, and the volume of this solution is taken as a standard, and then mixed with the cells. Optionally, when mixing the cells and the protective agent solution of the present disclosure, the cells is mixed according to the mass/volume ratio of 1:1. The protective agent of the present disclosure is preferably a phosphate buffer solution added with glucose, D-galactose and ascorbic acid, and the amount of the glucose, D-galactose, and ascorbic acid added is 2%, 2.5%, and 0.1% of the weight of the cells, respectively. The parameters of the vacuum freeze-drying of the present disclosure are preferably placing in a −35° C. environment to pre-freeze for 5 h, and then freeze-drying at −55° C. and vacuum degree of 5 pa for 24 h.

When the active ingredient of the scavenger is dead cells of *Lactobacillus helveticus* KD-3, the addition number of dead cells of *Lactobacillus helveticus* KD-3 to the scavenger is 0.5 g/L.

When the active ingredient in the scavenger is viable cells or lyophilized powder of the *Lactobacillus helveticus* KD-3, the number of viable bacteria count of the *Lactobacillus helveticus* KD-3 in the scavenger of the present disclosure is $\geq 1 \times 10^{11}$ CFU/g, more preferably $3.25 \times 10^{11}$ CFU/g. The scavenger of the present disclosure may be applied to heavy metal-contaminated water samples or foodstuffs Optionally, the operating temperature of the scavenger of the present disclosure is 32-40° C., preferably 34-38° C., more preferably 36-37° C.

The present disclosure provides a functional probiotic goat milk powder for removing heavy metals, and the functional probiotic milk powder includes a lyophilized powder prepared from the *Lactobacillus helveticus* D-3 of the above technical scheme.

Optionally, the viable bacteria count of the *Lactobacillus helveticus* KD-3 in the lyophilized powder of the present disclosure is $\geq 1\times 10^{11}$ CFU/g, more optionally $1\times 10^{11}$ CFU/g. The effective viable bacteria count of the *Lactobacillus helveticus* D-3 in the functional probiotic goat milk powder described herein is $\geq 3\times 10^7$ CFU/g, more preferably $3.25\times 10^7$ CFU/g.

The functional goat milk powder for removing heavy metals of the present disclosure removes cadmium, chromium and lead from the human body after consumption.

Optionally, the functional goat milk powder for removing heavy metals according to the present disclosure includes the *Lactobacillus helveticus* KD-3 goat milk powder. The preparation method of the *Lactobacillus helveticus* KD-3 goat milk powder according to the present disclosure preferably includes mixing the *Lactobacillus helveticus* KD-3 lyophilized powder and goat milk powder in equal increments under aseptic conditions to obtain the *Lactobacillus helveticus* KD-3 goat milk powder.

Optionally, the effective viable bacterial count of *Lactobacillus helveticus* KD-3 in the functional probiotic goat milk powder according to the present disclosure is $3.25\times 10^7$ CFU/g.

The *Lactobacillus helveticus* KD-3 goat milk powder of the present disclosure has a higher removal rate of lead and cadmium in an artificial intestinal fluid environment, reaching 56.31±1.72% and 23.87±1.97%, respectively; and the *Lactobacillus helveticus* KD-3 goat milk powder has a lower removal rate of lead and cadmium in artificial gastric fluids, at 24.12±1.34% and 12.02±0.98%, respectively.

The *Lactobacillus helveticus* KD-3 of in the present disclosure may be added directly to the reconstituted food to adsorb heavy metals in the food, where the food may remove cadmium, chromium and lead from the human body after being consumed, and the heavy metals are adsorbed onto the probiotic cells and excreted with the feces.

In order to further illustrate the present disclosure, the technical schemes provided by the present disclosure are described in detail below in connection with the accompanying drawings and embodiments, which are not to be construed as limiting the scope of protection of the present disclosure.

The compounds applied in the following embodiments with the addition of lead ion $Pb^{2+}$ are lead nitrate; the compounds applied with the addition of chromium ($Cr^{6+}$) are potassium dichromate, and the compounds applied with the addition of cadmium ($Cd^{2+}$) are cadmium nitrate. the MRS broth liquid medium and the MRS broth agar medium are both commercially available products. The cadmium removal rates in the present disclosure are all cadmium ion removal rates; lead removal rates are all lead ion removal rates, and chromium removal rates are all chromium ion removal rates.

Embodiment 1 Isolation, Screening and Characterization of *Lactobacillus helveticus* KD-3

1. Isolation of *Lactobacillus helveticus* KD-3

In the ultra-clean bench, the milk Kaifir grains purchased from Fushun, Liaoning Province are stirred under aseptic conditions, and MRS agar medium (lactic acid bacteria identification medium) with the addition of cadmium nitrate (the amount of cadmium nitrate added is 60 mg/kg) is used as the screening medium, and nine strains of cadmium resistant bacteria are obtained from them by screening using the plate isolation method, since the nine strains are isolated using the lactic acid bacteria identification medium, the colony morphology and Gram staining are preliminarily judged, and it is determined that all the 9 strains are lactic acid bacteria and are named S1, KD-3, S2, S3, S4, S5, S6, S7 and S8 respectively.

2. Screening of Lead-Resistant Lactic Acid Bacteria (1) A total of nine cadmium-resistant lactic acid bacteria strains S1, KD-3, S2, S3, S4, S5, S6, S7 and S8 obtained in step 1 are isolated and purified and cultured to obtain single colonies;

(2) lead nitrate (lead ion $Pb^{2+}$) mother liquor is diluted and added to 10 mL of different MRS broth liquid media, specifically:

treatment 1: lead-containing MRS broth liquid medium with a final lead concentration of 60 mg/L is prepared;

treatment 2: lead-containing MRS broth liquid medium with a final concentration of lead of 80 mg/L is prepared; and (3) single colonies of the nine cadmium-resistant lactic acid bacteria cultured in step (1) are inoculated to the culture medium of treatment 1 and treatment 2, respectively, and the dynamic change of pH value of the medium is monitored for the 0th, 12th, 15th, and 18th hour of the growth of the lactic acid bacteria, and the number of viable bacteria of each tested strain is determined by using the diluted spread plate method after 24 h of culture in an environment with high concentration of lead ions to judge the resistance of different species of lactic acid bacteria to lead ions.

Diluted spread plate method: the bacterial solution of treatment 1-treatment 2 after 24 h of culture is prepared into a homogeneous dilution, 1 mL is taken with a sterile syringe and evenly coated onto the MRS agar medium, and the viable bacteria are counted after 48 h, where the viable bacterial count of S1 is $(16\pm 1.93)\times 10^8$ CFU/mL, the viable bacterial count of S2 is $(2\pm 0.38)\times 10^8$ CFU/mL, the viable bacterial count of S3 is $(6\pm 1.06)\times 10^8$ CFU/mL, the viable bacterial count of S4 is $(48\pm 3.72)\times 10^8$ CFU/mL, the viable bacterial count of S5 is $(5\pm 1.06)\times 10^8$ CFU/mL, the viable bacterial count of S6 is $(3\pm 0.48)\times 10^8$ CFU/mL, the viable bacterial count of S7 is $(10\pm 2.09)\times 10^8$ CFU/mL, the viable bacterial count of S8 is $(29\pm 3.02)\times 10^8$ CFU/mL, and the viable bacterial count of KD-3 is $(76\pm 4.31)\times 10^8$ CFU/mL. The results are shown in FIG. 1. As can be seen from FIG. 1, the three strains (KD-3, S4 and S8) of lactic acid bacteria have better resistance to $Pb^{2+}$, and the resistance of the two strains, S2 and S6, are relatively poor; however, there are colonies growing on plates with high concentrations of lead, indicating that lactic acid bacteria have an auto-regulatory mechanism to attenuate the damage of $Pb^{2+}$ to the bacterium, therefore, the nine strains are all used in the $Cr^{6+}$ resistance screening test.

3. Screening of Chromium-Resistant ($Cr^{6+}$) Lactic Acid Bacteria

Treatment group 1: the nine cadmium-resistant lactic acid bacteria strains from step 1 are inoculated into MRS broth liquid medium containing potassium dichromate for culture, respectively, and the chromium ion concentration of MRS broth liquid medium is 300 mg/L;

Treatment group 2: the nine cadmium-resistant lactic acid bacteria strains mentioned above are inoculated into MRS broth liquid medium containing potassium dichromate for culture respectively, and the chromium ion concentration of MRS broth liquid medium is 500 mg/L;

Control group: 9 strains of cadmium-resistant lactic acid bacteria strains mentioned above are inoculated separately in chromium-free MRS broth liquid medium for culture.

The $OD_{600}$ values of the resulting cultures are determined after 24 h of culture in Treatment group 1, Treatment group 2 and Control group to calculate the inhibition rate.

Inhibition rate (%)=100%×[1−$OD_{600}$ (sample)/$OD_{600}$ (blank control)]

Figure 2:
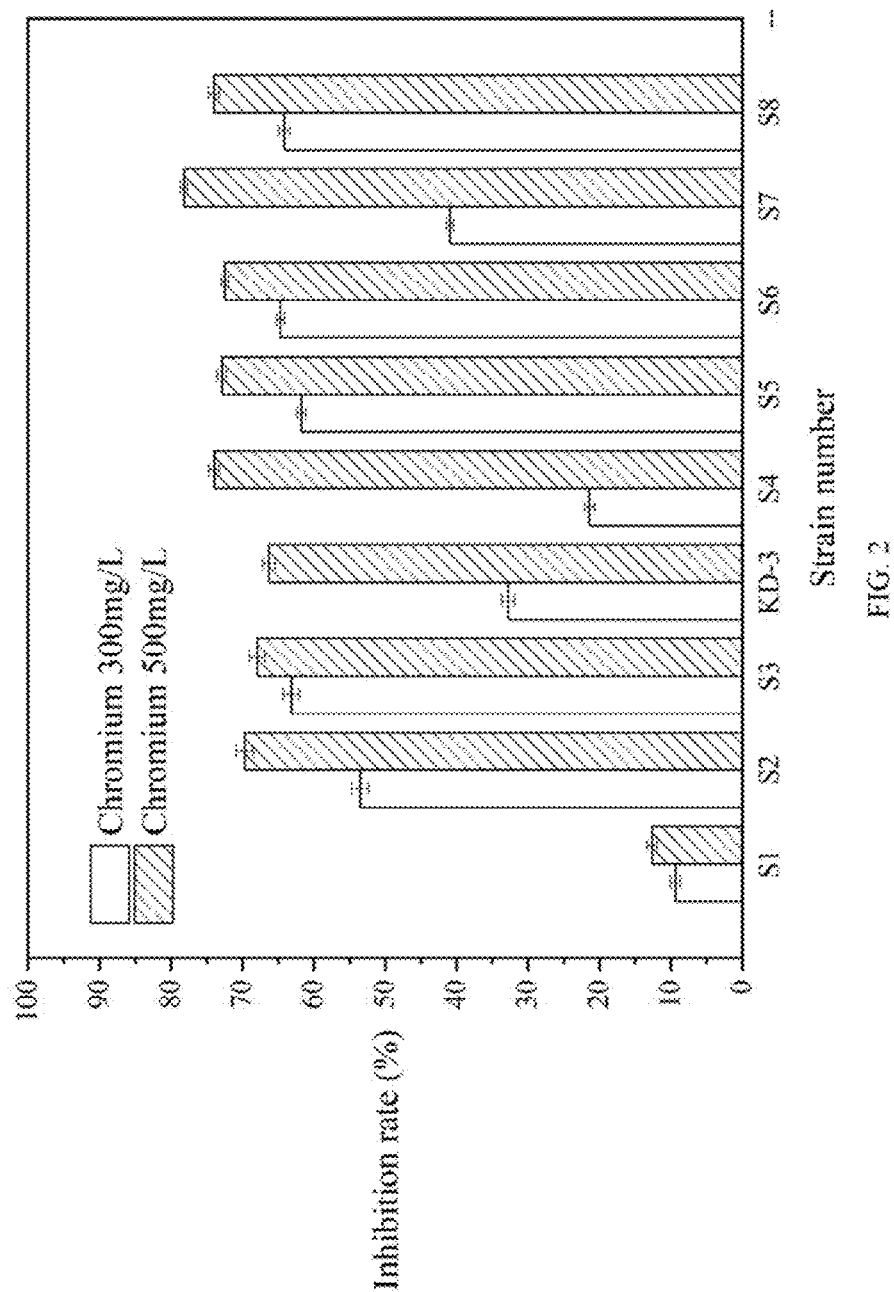
FIG. 2 shows the effect of high concentration of chromium salts on the growth of nine strains of lactic acid bacteria.

The results are shown in FIG. 2. Except for S1, the growth of all strains is significantly inhibited under high chromium concentration (500 mg/L), and the inhibition rate reaches more than 70%; at low chromium concentration (300 mg/L), the resistance of each strain to chromium shows significant variability; under the low chromium concentration (300 mg/L), the inhibition rate of chromium of the strains S1, S2, S3, KD-3, S4, S5, S6, S7 and S8 is 9.34±0.7%, 53.54±1.2%, 63.13±1.1%, 32.79±0.89%, 21.4±0.72%, 61.73±0.65%, 64.69±0.53%, 40.98±0.47, and 64.15±0.76, respectively; while under high chromium concentration (500 mg/L), the inhibition rate of chromium of the strains S1, S2, S3, KD-3, S4, S5, S6, S7 and S8 is 12.65±0.7%, 69.72±1.2%, 67.95±1.1%, 66.26±0.89%, 73.94±0.72%, 72.87±0.65%, 72.48±0.53%, 78.19±0.47%, and 73.97±0.76% respectively; at low chromium concentration (300 mg/L), three of the strains numbered S1, KD-3, and S4 show good chromium resistance with inhibition rates below 40%.

4. Determination of Minimum Inhibitory Concentration (MIC) of Compound Heavy Metal Resistant Bacterial Strains The medium is prepared by adding different concentrations of heavy metals $Cd^{2+}$, $Pb^{2+}$, $Cr^{6+}$ to MRS broth liquid medium. The composition of the medium is shown medium 1 to medium 5 of Table 1.

S1, KD-3, S2, S3, S4, S5, S6, S7, S8 bacterial cultures are selected respectively, and after diluting a certain number of times, 1 mL is taken and coated on the plates of medium 1 to medium 5, and the growth is observed by counting the viable bacteria after 48 h, and the results are shown in Table 1. According to Table 1, it is observed that in the composite metal environment of medium 5, the concentrations of $Pb^{2+}$, $Cd^{2+}$, and $Cr^{6+}$ are 1500 mg/L, 150 mg/L and 1500 mg/L, respectively, where only three strains numbered S8, S2, and KD-3 grow; since the number of colonies obtained from KD-3 cultured in medium 5 is more than that of S8, the order of resistance of the nine strains to the compound heavy metals derived from the combined minimum inhibitory concentration is: KD-3, S8, S2, S4, S5, S1, S3, S7, and S6. There is no growth of S3 and S6 in the culture broth. Therefore, the resistant strains in the initial screening are KD-3, S8, S2, S4, S5, S1, and S7.

TABLE 1

MIC results of compound heavy metal resistant strains

| S/N of strains | | Heavy metal concentration (mg/L) | | | | |
| --- | --- | --- | --- | --- | --- | --- |
| | | Medium 1 | Medium 2 | Medium 3 | Medium 4 | Medium 5 |
| | $Pb^{2+}$ | 0 | 100 | 500 | 1000 | 1500 |
| | $Cd^{2+}$ | 0 | 30 | 50 | 100 | 150 |
| | $Cr^{6+}$ | 0 | 100 | 500 | 1000 | 1500 |
| S8 | | +++ | +++ | +++ | +++ | ++ |
| S2 | | +++ | +++ | ++ | ++ | + |
| S4 | | +++ | +++ | ++ | + | − |
| S6 | | +++ | +++ | + | − | − |
| S3 | | +++ | +++ | + | − | − |
| S5 | | +++ | +++ | +++ | ++ | − |
| S1 | | +++ | +++ | + | + | − |
| KD-3 | | +++ | +++ | +++ | +++ | ++ |
| S7 | | +++ | +++ | + | − | − |

Note:
"+++" indicates that the colony number reaches 100-300 CFU/mL; "++" indicates that the colony number is in the range of 10-100 CFU/mL; "+" indicates that the colony number is in the range of 0-10 CFU/mL; "−" indicates that there is no colony growth on the plate.

5. Testing of Heavy Metal Adsorption Properties of Resistant Bacteria Strains

Single heavy metal adsorption capacity of the screened resistant strains is tested separately using atomic absorption spectrometry (AAS).

(1) Plotting of Standard Curves for Three Heavy Metals

Cadmium ($Cd^{2+}$) standard curve: 37.5 μL of 1000 mg/L of cadmium standard solution is taken and fixed to 50 mL, that is, a cadmium solution of 0.75 mg/L; the above cadmium solution is taken 8, 6, 4, 2 mL respectively and added to 2, 4, 6, 8 mL of ultrapure water, and then fixed to 10 mL respectively, and then the samples with concentrations of 0.6, 0.45, 0.3, 0.15 mg/L are prepared respectively, and the absorbance is measured by flame atomic spectrophotometer, the standard curve of cadmium is plotted. The cadmium standard curve: y=0.0463x−0.0023, $R^2$=0.9994.

Lead ($Pb^{2+}$) standard curve: 1 mL of 1000 g/mL lead standard solution is taken and add with 9 mL water to prepare a 100 mg/L lead solution, from which 2, 1.6, 1.2, 0.8, 0.4 mL are taken and added with 8, 8.4, 8.8, 9.2, 9.6 mL water respectively to prepare a series of lead ion solutions of 20, 16, 12, 8, 4 mg/L, respectively. The absorbance is measured and the lead standard curve is plotted. Lead standard curve: y=0.0209x−0.0037, $R^2$=0.9986.

Chromium ($Cr^{6+}$) standard curve: 125 μL of chromium standard solution of 1000 g/mL is taken and added with water to fix to 50 mL, that is, a chromium ion solution of 2.5 mg/L, where 8, 6, 4, 2 mL is respectively taken form the 50 mL, and added with 2, 4, 6, 8 mL of water respectively to prepare a series of chromium solutions of 2.0, 1.5, 1, 0.5 mg/L, respectively, and the chromium standard curve is plotted; the chromium standard curve: y=0.0427x−0.0023, $R^2$=0.9997.

(2) Measurement of Heavy Metal Adsorption Capacity

Treatment group 1: the initial screening of resistant strains KD-3 are inoculated to the MRS broth liquid medium containing cadmium ions at 60 mg/L in accordance with the inoculum amount of 5% (v/v), respectively, then the pH of the culture broth is determined after culture at 37° C. for 24 h; the obtained culture broth is centrifuged at 8000 rpm for 10 min to determine the mass of the cells; the supernatant after centrifugation is taken and added into a microwave digestion device, then 5 mL of nitric acid is added and covered to stand for 5 min, then the digestion is carried out in accordance with the standard steps of the instrument in sequence (digestion for 10 min at 120° C., digestion for 15 min at 150° C., and digestion for 25 min at 190° C., respectively), followed by taking out after cooling and then heating up in a water bath at 100° C. for 30 min, and the volume is fixed with water into 10 mL. After the volume is fixed, 1 mL is taken and added to 9 mL of water, then filtered using a 0.45 m sterile filter membrane and placed into a 10 mL centrifuge tube, the KD-3 samples to be tested are kept separately in a refrigerator at 4° C., with three parallel experiments set up. The preparation of S2 samples to be tested, S4 samples to be tested, S5 samples to be tested, S1 samples to be tested, S8 samples to be tested, and S7 samples to be tested are same as the method of KD-3 samples to be tested.

The MRS broth liquid medium containing cadmium ions at 60 mg/L without bacterial addition is used as a blank control, and three parallel experiments are set up.

The samples to be tested of the above strains are measured by flame atomic spectrophotometer to determine the absorbance value of each sample, each sample has 3 times of parallel; the residual concentrations of $Cd^{2+}$, $Pb^{2+}$ and $Cr^{6+}$ in the samples to be tested are calculated by taking into the standard curves of lead, chromium and cadmium. After obtaining the residual concentration, the removal rate and adsorption amount are calculated as follows:

removal rate (%)=100×($C_0$−$C_1$)/$C_0$;adsorption amount=($C_0$−$C_1$)/m×V;

where $C_0$ (mg/L) represents the initial metal ion concentration in the solution; $C_1$ (mg/L) represents the metal residual concentration in the supernatant after adsorption; m is the mass of the cells (g); and V represents the volume of the solution (L).

The pH of the culture solution and the mass of the cells are determined to compare the growth of lactic acid bacteria in the process of binding metals.

Figure 3:
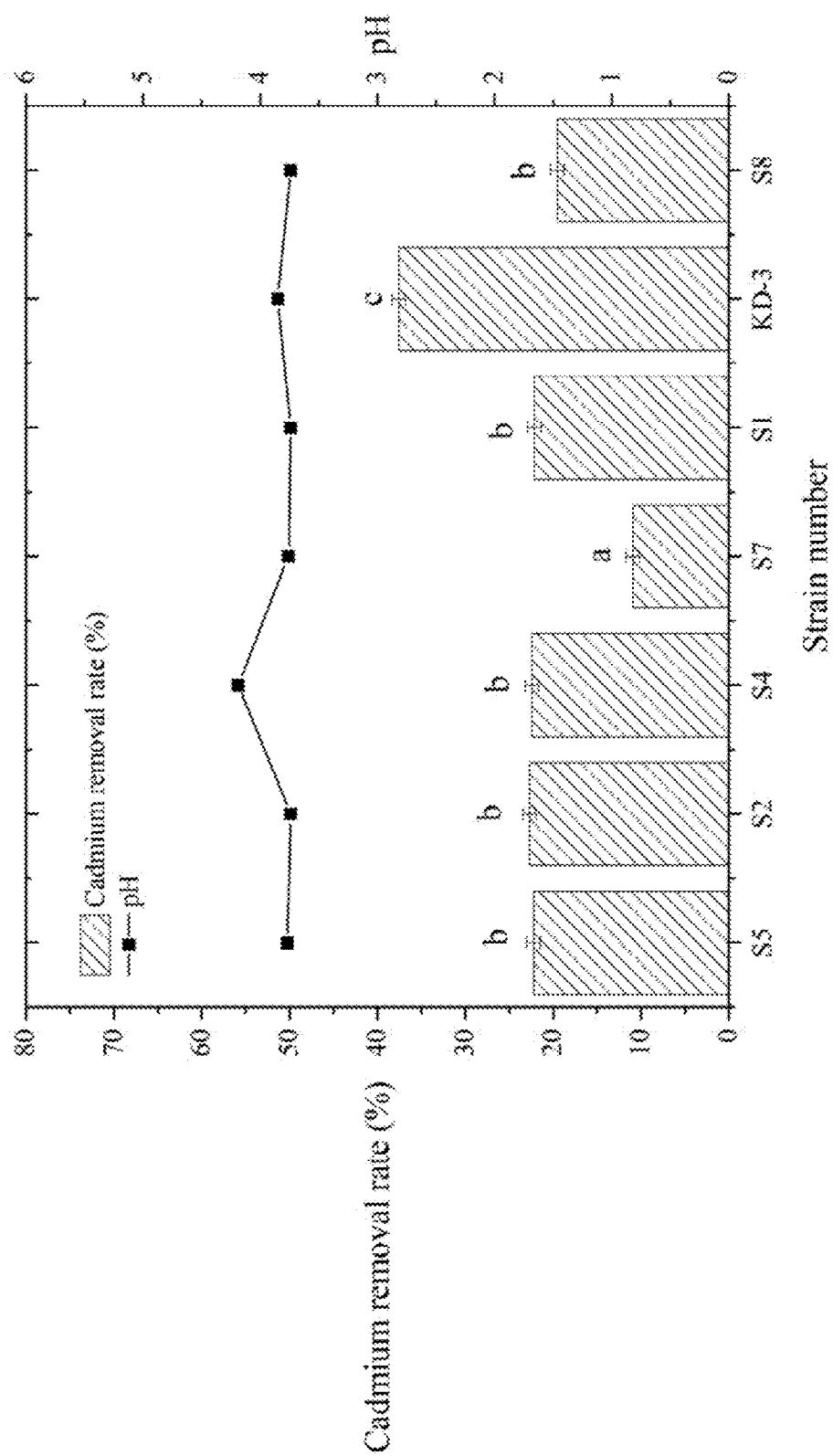
FIG. 3 shows the adsorption of lactic acid bacteria at 60 mg/L cadmium concentration.

Cadmium removal rate by lactic acid bacteria in MRS broth liquid medium is determined by atomic absorption spectroscopy; as shown in FIG. 3, the cadmium removal rate of strains S5, S2, S4, S7, S1, KD-3, and S8 are 22.22±0.76%, 22.67±0.71%, 22.41±0.73%, 10.92±0.56%, 22.13±0.69%, 37.54±0.85%, and 19.53±0.62%, respectively, where the KD-3 shows the best cadmium removal, with removal rate reaching 37.54±0.85% and adsorption amount reaching 159 mg/g; the strain with the lowest removal rate is S7, being 10.92±0.56%, and the adsorption amount is only 28 mg/g; the cadmium removal rates, in descending order, are as follows: KD-3, S2, S4, S5, S1, S8, and S7. The pH value of the culture solution after adsorption is used to characterize the growth of the bacteria, and the pH value of the culture solution of strains S5, S2, S4, S7, S1, KD-3, and S8 is 3.77±0.04, 3.74±0.03, 4.19±0.07, 3.76±0.05, 3.74±0.04, 3.85±0.06, 3.74±0.02, respectively. According to from FIG. 3, the cadmium ion has a greater effect on the growth of strain S4.

Treatment group 2: same as treatment group 1, the only difference is that the initially screened resistant strains KD-3, S2, S4, S5, S1, S8, S7 are inoculated to MRS broth liquid medium containing 60 mg/L of lead ions according to the inoculum amount of 5% (v/v) for culture, respectively.

The pH value of the culture solution and the mass of the bacteria are determined to compare the growth of lactic acid bacteria in the process of binding metals.

Figure 4:
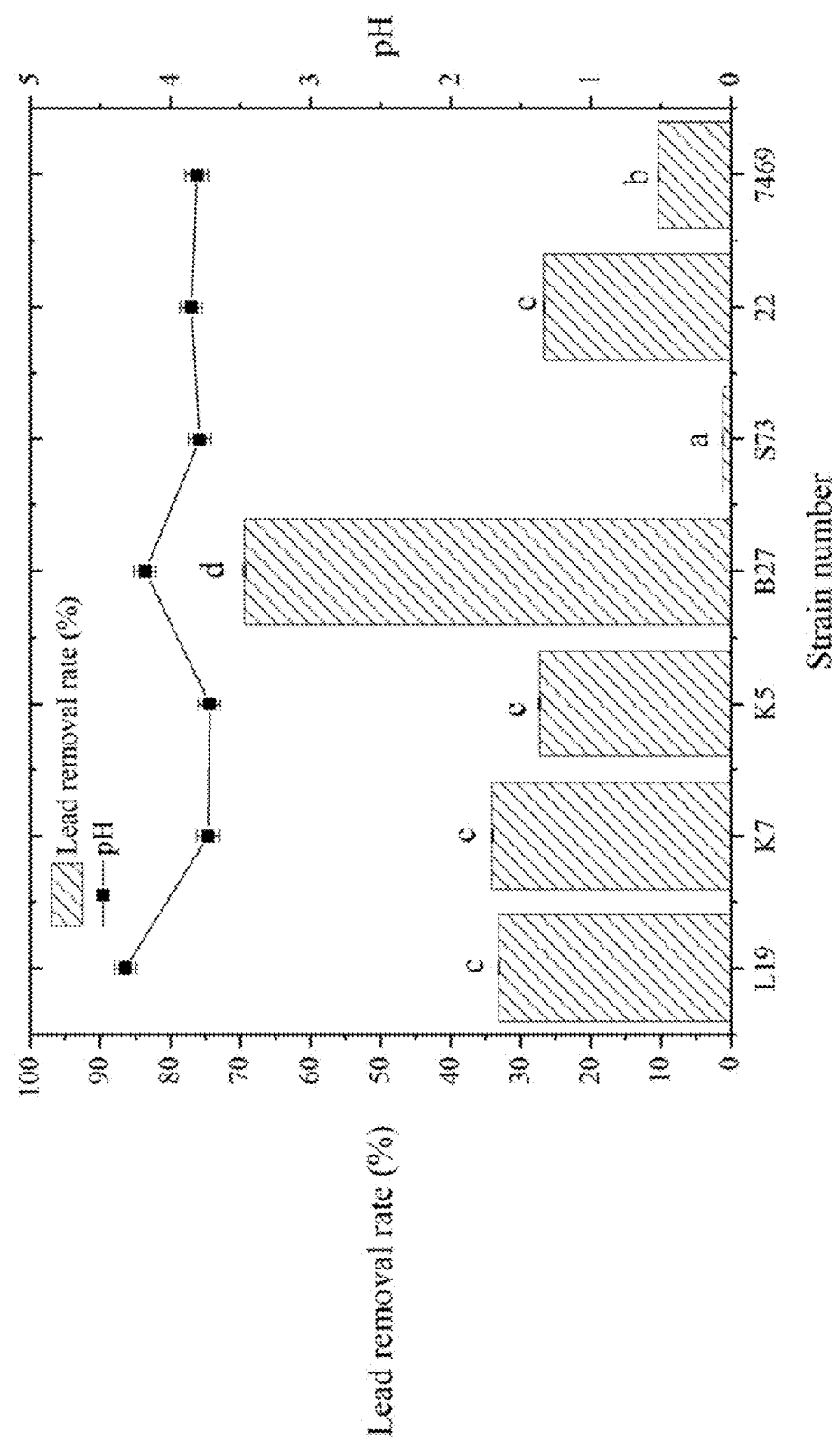
FIG. 4 shows the lead adsorption by lactic acid bacteria at 60 mg/L metal concentration.

Analysis of the effect of KD-3 on the adsorption of lead ions $Pb^{2+}$ (see FIG. 4 and Table 2) show that the strain S2 has the best adsorption of lead ions, with a removal rate of 69.41±0.19% and an adsorption amount of 247 mg/g; the removal rate of KD-3 reaches 34.01±0.57%, with an adsorption amount of 142 mg/g, and the worst one is strain S7, with a removal rate of 1.11±0.09%; the strains are ranked in terms of adsorption effects as follows: S2, KD-3, S1, S8, S4, S5, and S7. From the results of the pH measurements, it is clear that lead ions have a significant effect on the growth of S2 and S1, while the growth of the remaining strains is not significantly affected.

TABLE 2

Data on the effect of adsorption of lead ions by strain KD-3

| S/N of strains | Lead removal rate (%) | Standard deviation | pH | Standard deviation |
|---|---|---|---|---|
| S1 | 33.1 | 0.37 | 4.32 | 0.15 |
| KD-3 | 34.01 | 0.57 | 3.73 | 0.08 |
| S8 | 27.26 | 0.43 | 3.72 | 0.06 |
| S2 | 69.41 | 1.59 | 4.18 | 0.11 |
| S7 | 1.11 | 0.08 | 3.79 | 0.07 |
| S4 | 26.66 | 0.18 | 3.85 | 0.09 |
| S5 | 10.32 | 0.12 | 3.81 | 0.08 |

Treatment group 3: same as treatment group 1, the only difference is that the initially screened resistant strains KD-3, S2, S4, S5, S1, S8, and S7 are inoculated to MRS broth liquid medium containing chromium ions of 60 mg/L according to an inoculum amount of 5% (v/v), respectively.

The pH value of the culture solution is determined to compare the growth of lactic acid bacteria during metal binding.

Figure 5:
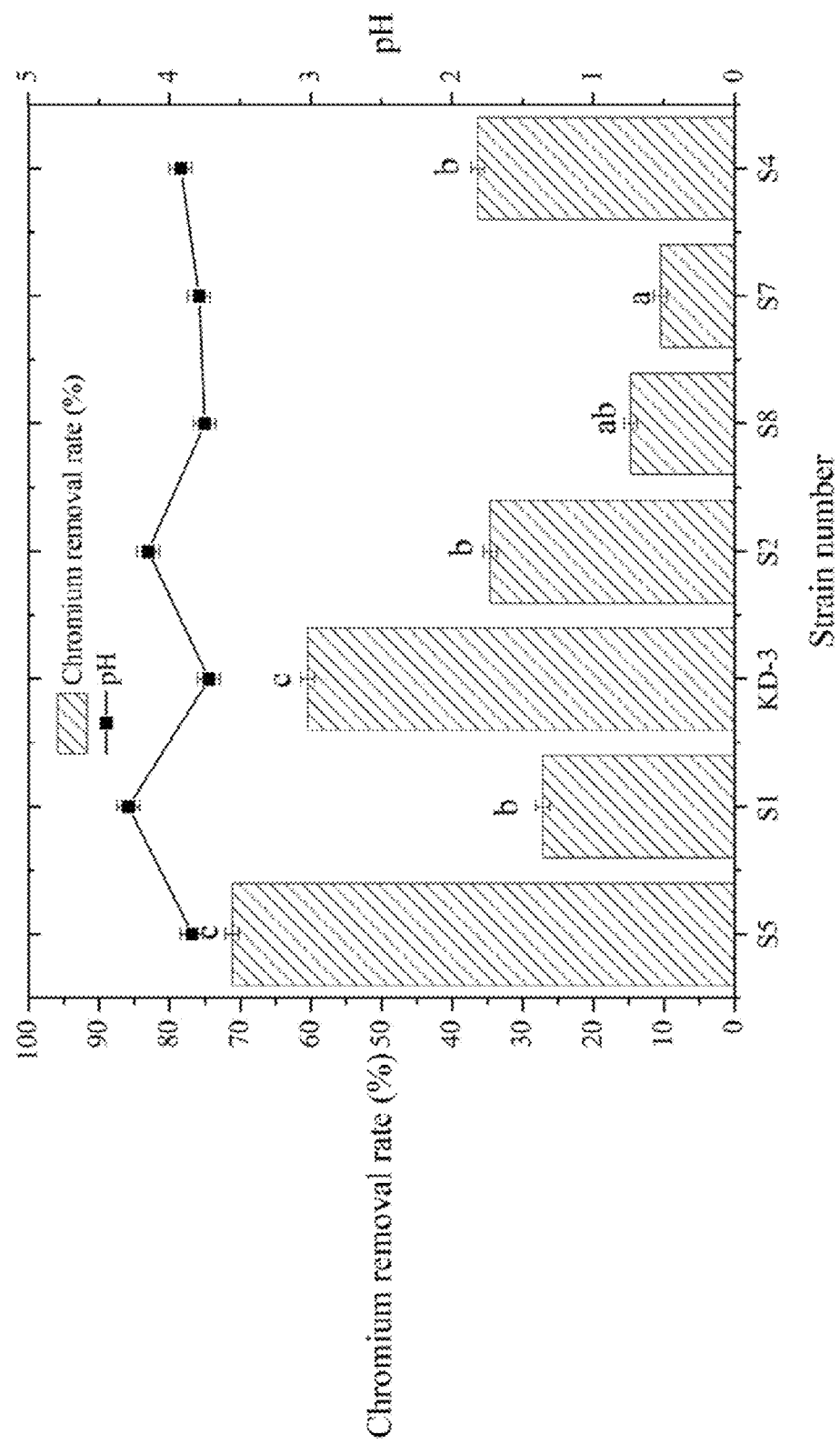
FIG. 5 shows the chromium adsorption by different strains at 60 mg/L metal concentration.

From the results of adsorption of chromium ions by lactic acid bacteria (FIG. 5), it may be seen that the chromium removal rates of S5, S1, KD-3, S2, S8, S7 and S4 are 71.13±0.97%, 27.15±0.56%, 60.44±1.28%, 34.57±0.79%, 14.71±0.85%, 10.49±0.38%, 36.32±0.73%, where the strain S5 has the best chromium adsorption, with a removal rate of 71.13±0.97%, and an adsorption amount of 342 mg/g; the chromium removal rate of strain KD-3 is 60.44±1.28% and the adsorption amount is 207 mg/g; strain S7 has the worst adsorption performance with a removal rate of 10.49±0.67%, and an adsorption amount of 9.76 mg/g; the comprehensive chromium removal rate is ranked as: S5, KD-3, S4, S2, S1, S8, and S7. The pH values of the culture solution of strains S5, S1, KD-3, S2, S8, S7, and S4 are 3.84±0.08, 4.29±0.11, 3.72±0.06, 4.15±0.09, 3.75±0.05, 3.79±0.07, and 3.92±0.1, respectively. According to the measurement results of pH value, lead ions have a significant effect on the growth of S2 and S1, while the growth of the rest of the strains is not significantly affected.

6. Determination of Acid-Producing Capacity and Antioxidant Capacity of Resistant Lactic Acid Bacteria (1) Acid-Producing Capacity Test KD-3, S2, S4, S5, S1, S8 and S7 are inoculated into MRS broth liquid medium for 24 h to obtain lactic acid bacteria fermentation solution, respectively. The lactic acid bacteria fermentation solution is centrifuged at a high speed of 8000 rpm for 15 min, and a certain amount of the supernatant is diluted and added into the biosensor, so that the lactic acid yield in the fermentation solution may be measured.

(2) Measurement of DPPH Radical Removal Rate

Treatment group: the resistant strains KD-3, S2, S4, S5, S1, S8 and S7 obtained from the screening of lactic acid fermentation broth in step (1) are centrifuged at 10,000 rpm for 15 min at low temperature (4° C.) to obtain the cells precipitate, then washed three times repeatedly with phosphate buffer solution (PBS) with pH of 7.2, and finally resuspended in PBS to obtain the cells; the cellular concentration of the resistant strains in the cells reaches $1.0 \times 10^9$ CFU/mL; 1 mL of the cells is taken and added to the freshly prepared DPPH anhydrous ethanol solution at 1:1 (v/v);

Control group: 1 mL DPPH anhydrous ethanol solution mixed with 1 mL phosphate buffer solution is used as control;

Both treatment and control groups are kept at room temperature and protected from light for 30 min, followed by centrifugation at 8000 rpm for 10 min, and the absorbance value of the samples at 517 nm is determined, and the DPPH radical removal rate is calculated as follows:

$$\text{DPPH removal rate (\%)} = 100\% \times [1 - A_{517} \text{ (experimental group)}/A_{517} \text{ (control group)}]$$

Figure 6:
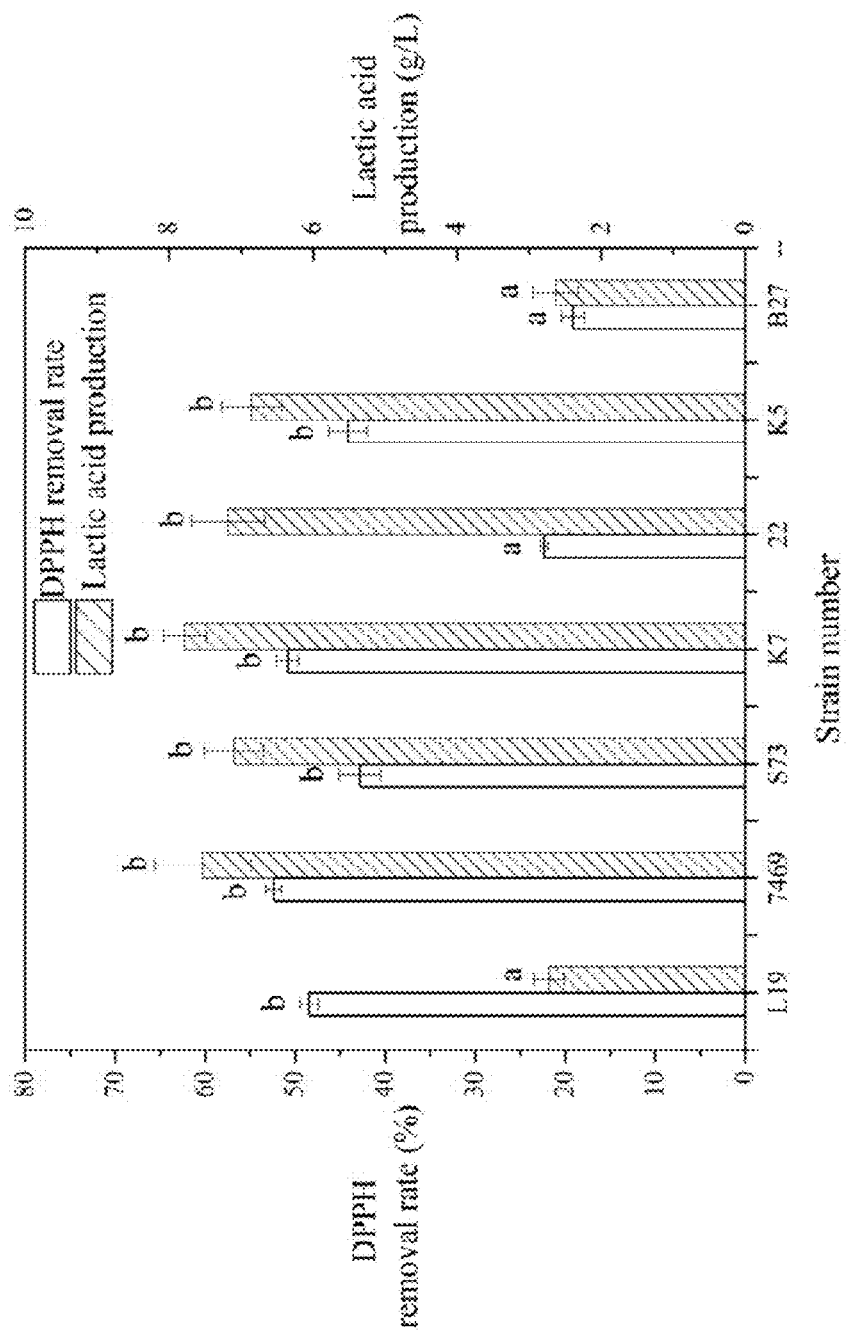
FIG. 6 shows the 2,2-Diphenyl-1-picrylhydrazyl (DPPH) removal and lactic acid production of different strains.

The DPPH radical removal rate and lactic acid production of the tested strains are measured to characterize the antioxidant capacity as well as the practical application potential of the strains as shown in FIG. 6. The DPPH radical removal rates of strains S1, S5, S7, KD-3, S4, S8, and S2 are (48.41±1.01)%, (52.38±0.89)%, (42.82±2.31)%, (50.81±1.23)%, (22.32±0.41)%, (44.11±2.11)%, (19.1±1.28)%, while the lactic acid production of strains S1, S5, S7, KD-3, S4, S8, and S2 are (2.72±0.21) g/L, (7.53±0.67) g/L, (7.1±0.41) g/L, (7.78±0.3) g/L, (7.18±0.51) g/L, (6.85±0.42) g/L, and (2.63±0.31) g/L, and the DPPH radical removal rates of strains S5, KD-3, 51, and S8 are significantly higher than those of strains S4 and S2; the lactic acid yields of strains KD-3, S5, S7, S4, and S8 are all greater than 6 g/L. Among them, the two indexes of strains S5 and KD-3 are higher than those of other tested strains.

Embodiment 2 Resistant Gene Detection

Five strains S8, S7, KD-3, S5 and S2 with triple heavy metal resistance and good adsorption performance are selected for the resistant gene detection test.

1. Primer Design and Synthesis

Based on the currently reported sequences of heavy metal resistant genes of microorganisms, three pairs of primers are designed and synthesized, including the czcD gene for resistance to the heavy metal cadmium, the pbrT gene for resistance to the heavy metal lead, and the chrA gene for resistance to the heavy metal chromium, and then the total DNA of the resistant strains is amplified with the above genes, the products of fluorescence quantitative PCR are designed, and the causes of the formation of resistance in lactic acid bacteria are investigated by absolute quantitative fluorescence PCR.

For resistant gene pbrT, the primers are pbrT-F: AGCGCGCCCAGGAGCGCAGCGTCTT (SEQ ID NO. 2); and pbrT-R: GGCTCGAAGCCGTCGAGRTA (SEQ ID NO. 3);

for resistant gene chrA, the upstream primer is chrA-F: TGGCTCTCGCTGTTCTTTGT (SEQ ID NO. 4); and the downstream primer is chrA-R: TAAGTGCGACAAGGGCAACT (SEQ ID NO. 5);

for resistant gene czcD, the upstream primer is czcD-F: TCATCGCCGGTGCGATCATCAT (SEQ ID NO. 6); and the downstream primer is czcD-R: TGTCATTCACGACAT-GAACC (SEQ ID NO. 7).

2. Qualitative Testing

Figure 7:
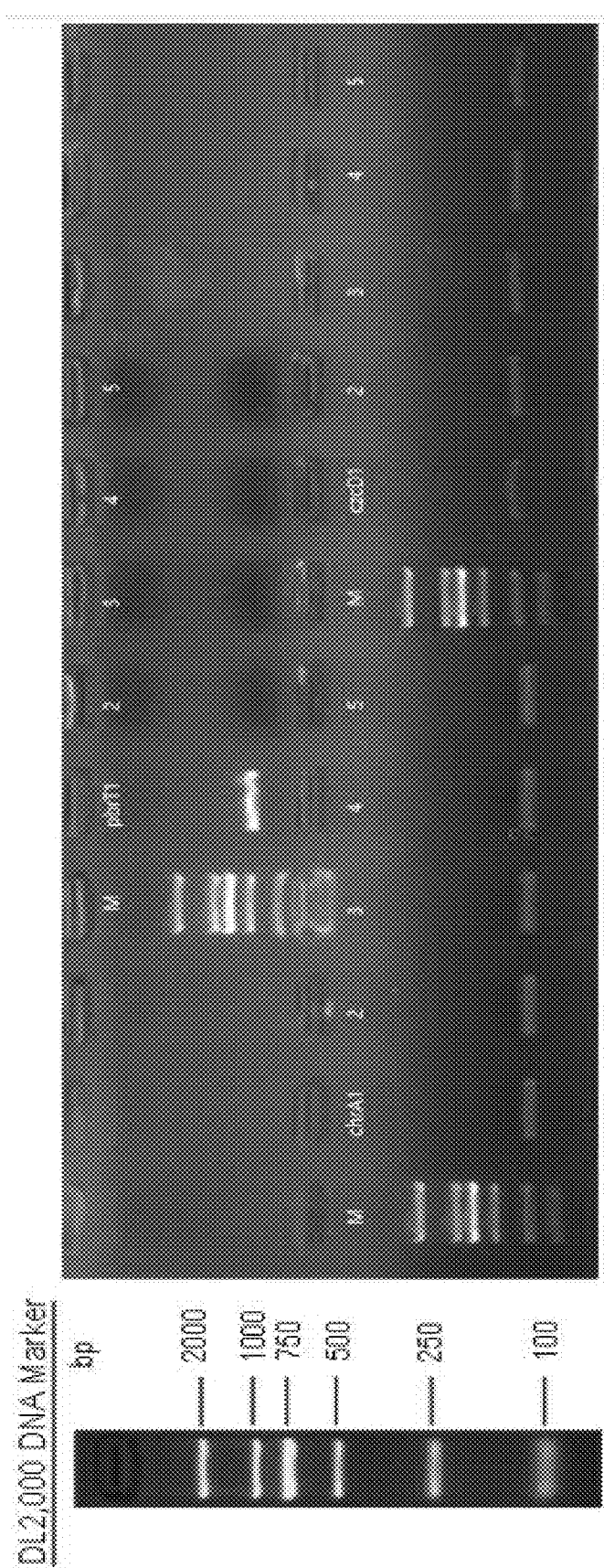
FIG. 7 shows the results of PCR amplification of three heavy metal resistant genes, where 1, 2, 3, 4 and 5 denote strains KD-3, S7, S8, S5 and S2, respectively.
Figure 8A:
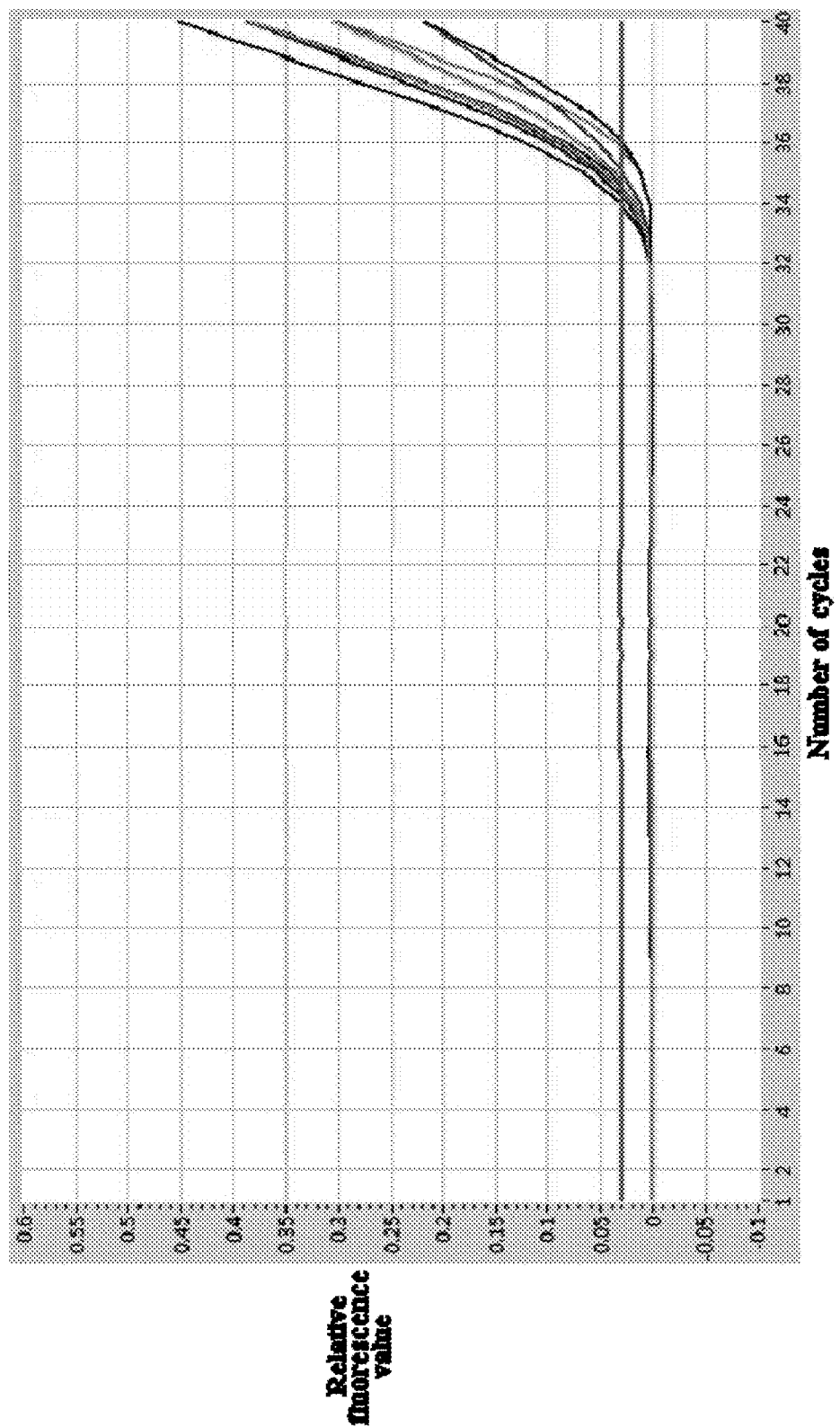
FIG. 8A shows the amplification curves of the resistant genes chrA.
Figure 8B:
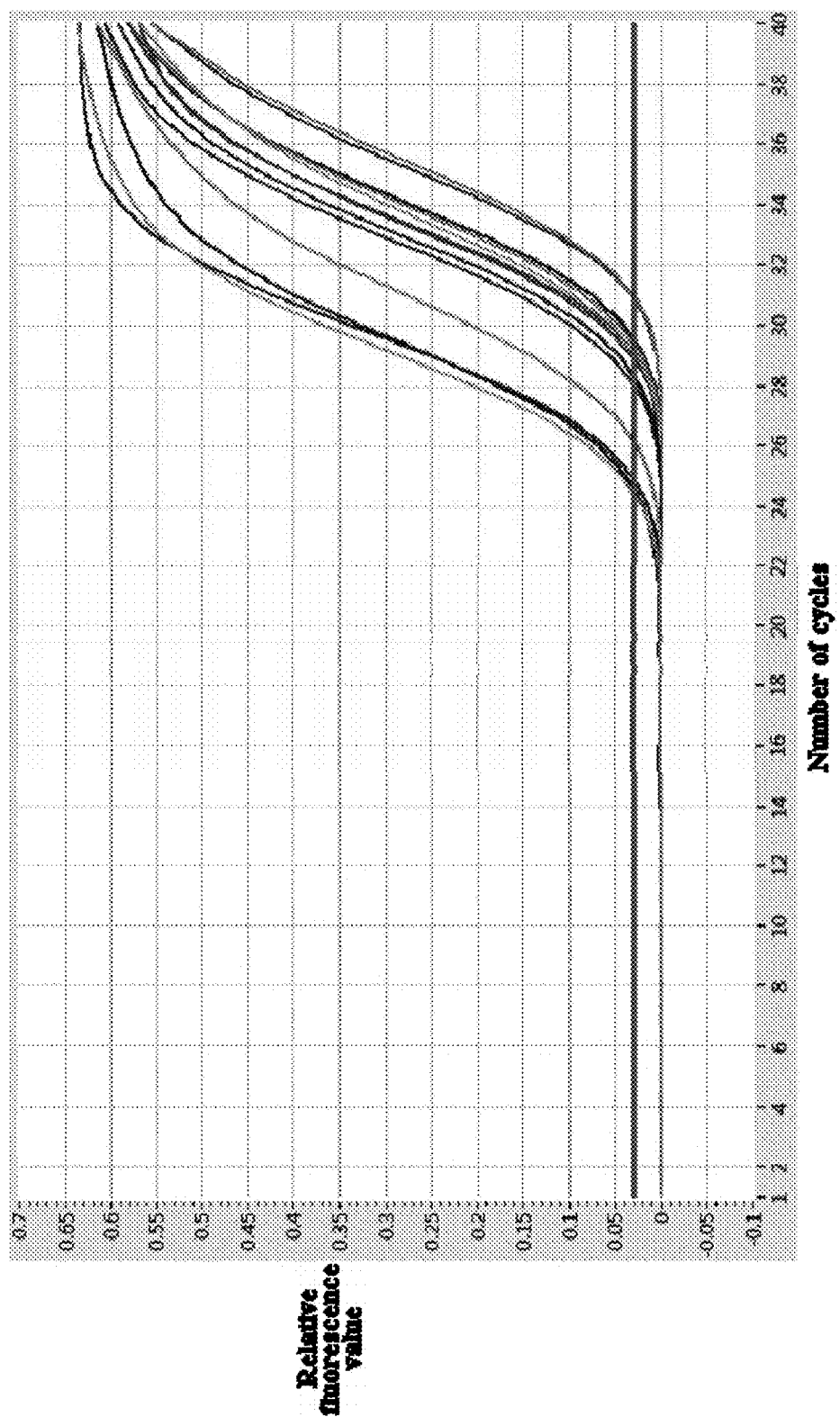
FIG. 8B shows the amplification curves of the resistant genes czcD.
Figure 8C:
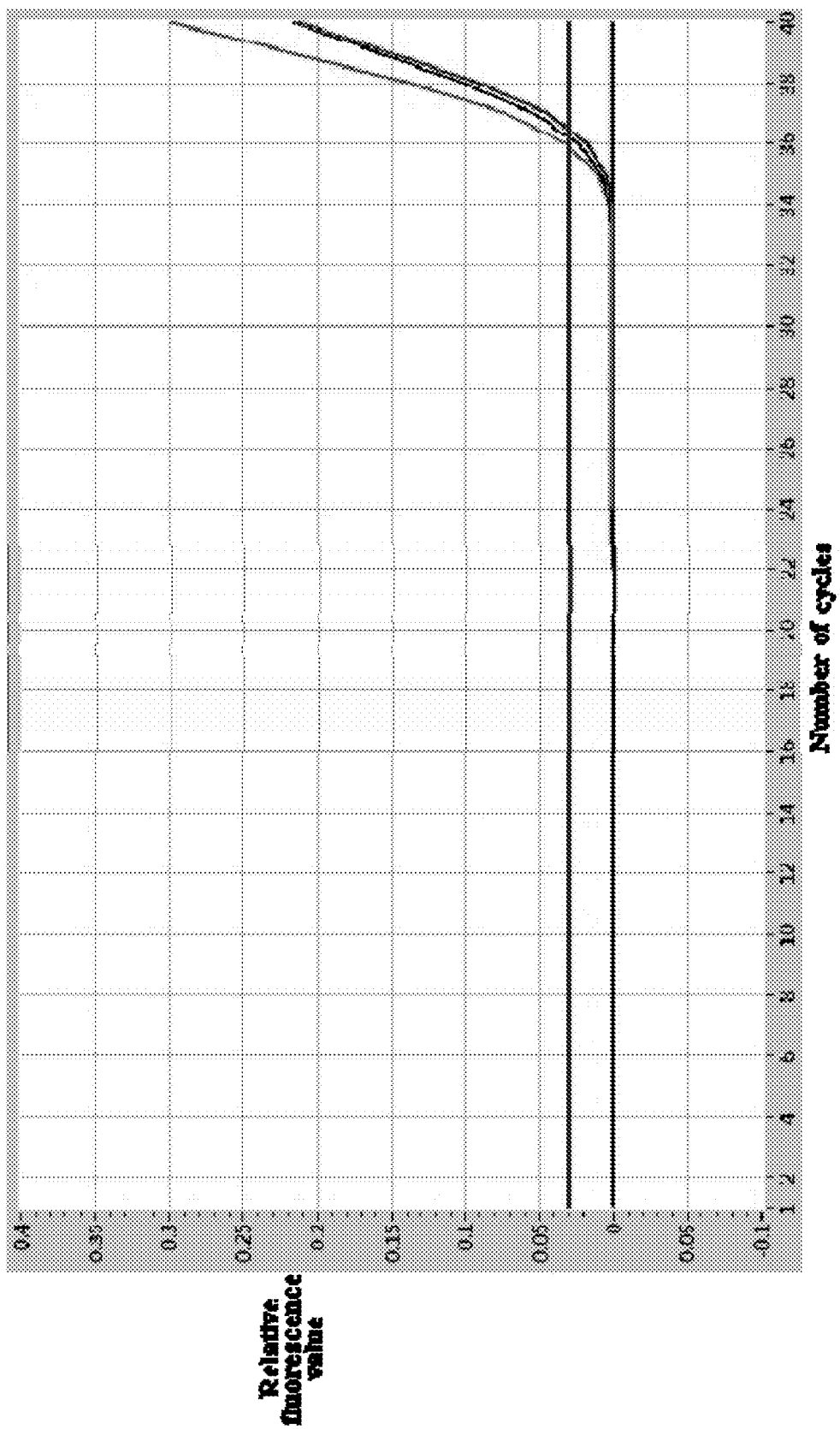
FIG. 8C shows the amplification curves of the resistant genes pbrT.
Figure 8D:
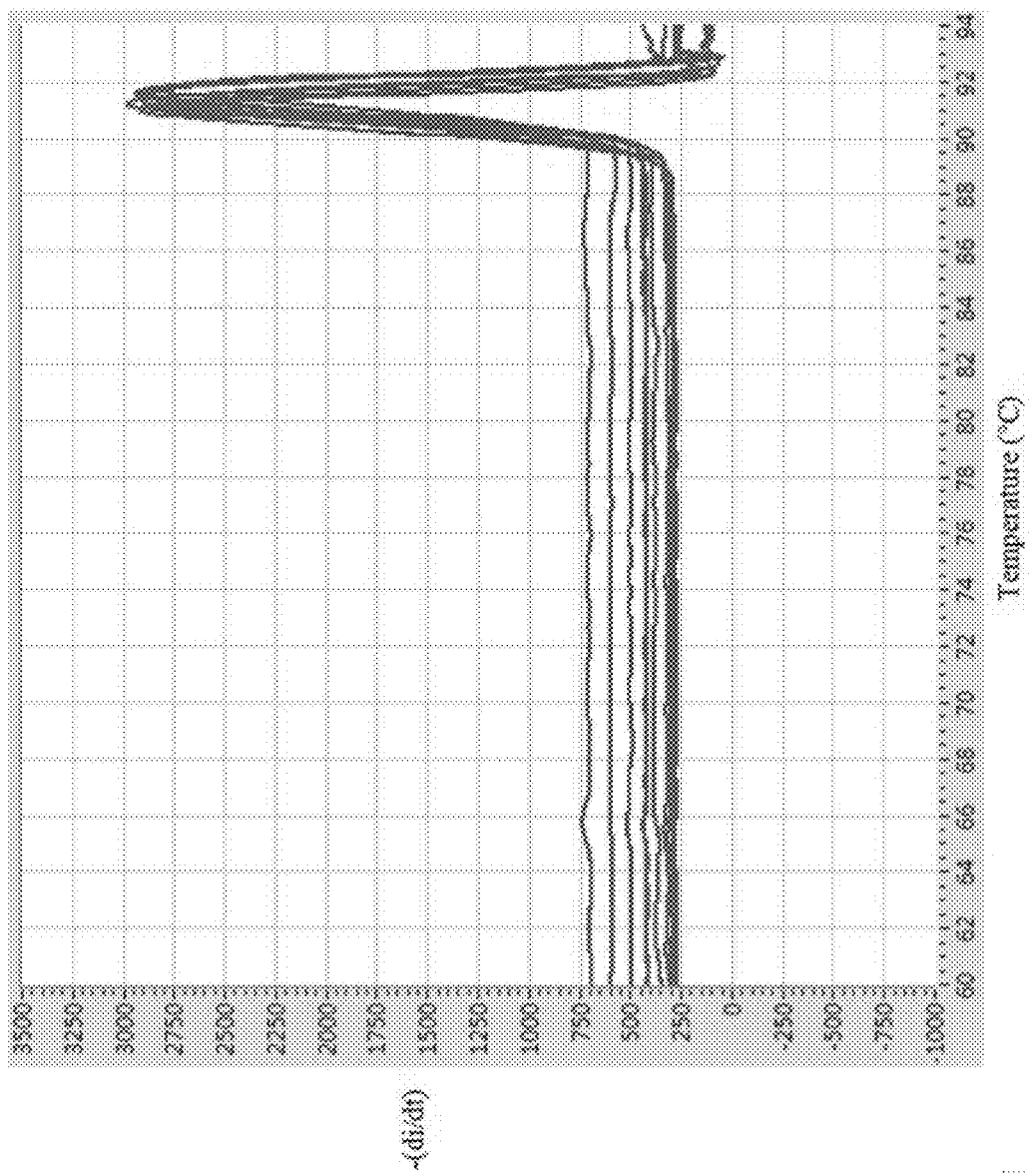
FIG. 8D shows the lysis curves of the resistant genes chrA.
Figure 8E:
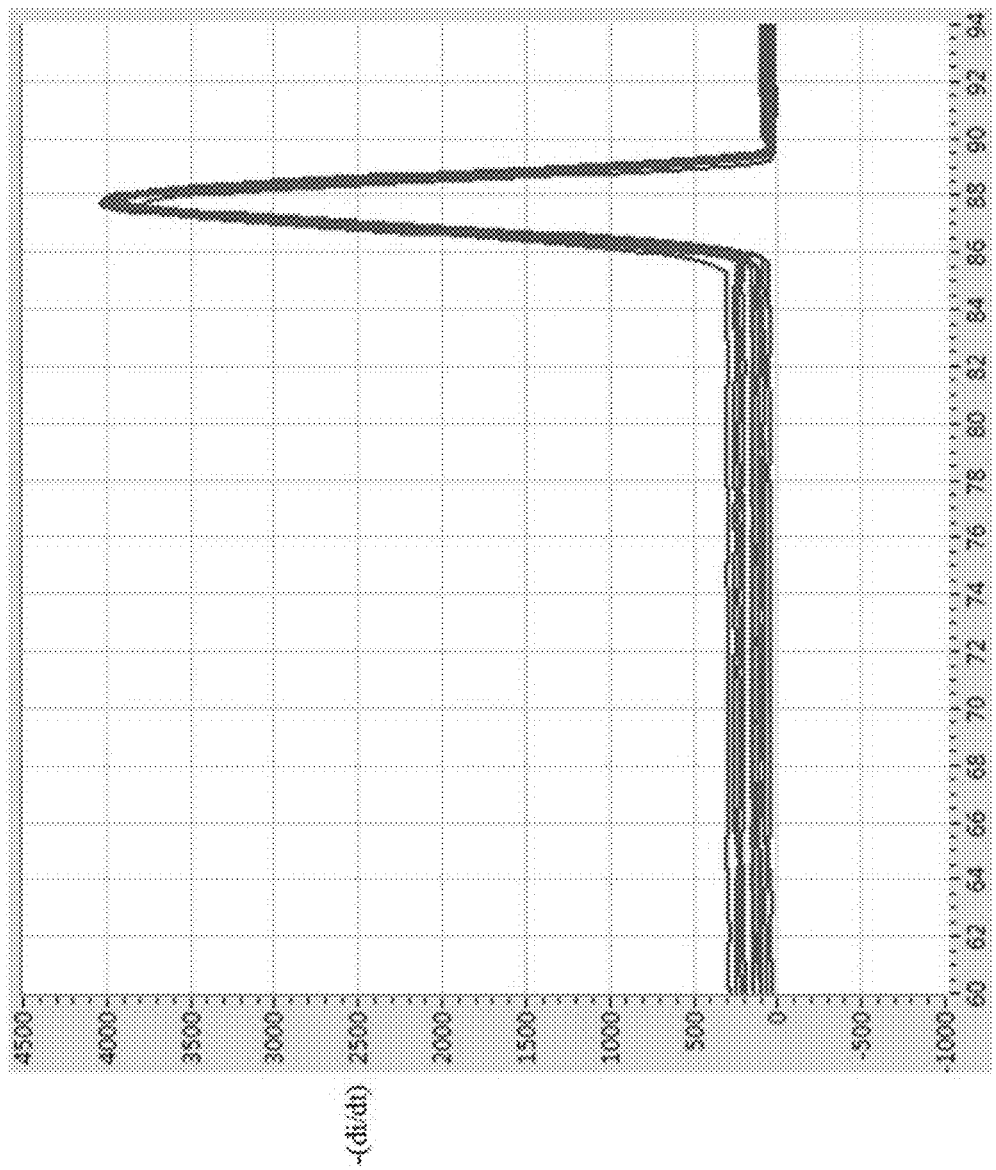
FIG. 8E shows the lysis curves of the resistant genes czcD.

Total DNA of each resistant strain S8, S7, KD-3, S5, and S2 is extracted and then amplified by absolute quantitative fluorescence PCR using the primers for the resistant genes from step 1, and gene fragments matching expectations are obtained by agarose gel electrophoresis (FIG. 7).

As may be seen from FIG. 7, both lead, cadmium and chromium resistant genes are present in the strain numbered KD-3, and both cadmium and chromium resistant genes are present in strains S2, S5, S7 and S8.

3. Quantitative Testing (1) Standard Construction

The specific steps are as follows: 1) obtaining the target fragments of lead, cadmium and chromium resistant genes using the primers of step 1; 2) purifying the target fragments; 3) ligation of target fragments; preparing the following DNA solution in sterile PCR tubes with a full volume of 5 μL; ligation reaction system components: pMD18-T Vecter (50 ng/μL) 1 μL, Insert DNA (target fragment) 1-2 μL, supplement to 5 μL using ddH$_2$O; 4) transformation of receptor *Escherichia coli* cells; 5) recovery: using 2YT medium for recovery; 6) plate coating; 7) picking a single colony for inoculation and culture; 8) bacterial testing; adding various components in a sterile PCR tubule according to the system of Table 3; extracting plasmid from bright bands in electrophoresis 9) plasmid extraction; suspending bacterial solution with sufficient oscillation, centrifuging and adding the Buffer, and carrying out plasmid extraction; (10) sequencing; according to the manual of the plasmid extraction kit to add samples for sequencing, using the NanoDrop 2000 to determine the concentration and purity of the plasmid. The number of copies of the resistant gene carried by the plasmid is derived by converting the concentration of the plasmid. The plasmid is used as a standard after a 10-fold serial dilution.

TABLE 3

| | Composition of PCR reaction system | | | | | | |
|---|---|---|---|---|---|---|---|
| System composition | Bacterial solution | M13F-47 | M13R-48 | 10× Buffer | dNTP | Taq enzyme | ddH$_2$O |
| Volume/μL | 3 | 0.5 | 0.5 | 1 | 0.5 | 0.25 | 4.25 |

(2) Repeatability and Stability Test of Fluorescent Quantitative PCR Method

The prepared standards are diluted to establish the amplification curve and the lysis curve, see FIG. 8A-FIG. 8F. The linear relationship that exists for the amplification reaction may be obtained by the known concentration of the standards. As observed from FIG. 8A-FIG. 8F, the dissolution curves of the three resistant genes all show a single peak, and the amplification products are homogeneous, with no specific peaks appearing, which is in line with the requirements of the test, and the results are stable and reliable.

4. Establishment of Real-Time PCR Standard Curves for Three Heavy Metal Resistant Genes The plasmid obtained from step (1) in the quantitative testing is used to perform the 10-fold serial dilution to obtain a template of eight gradients, each is repeated three times; a standard curve is plotted based on the Ct values and the amplification curves. The linear relationship that exists in the amplification reaction may be obtained by the known concentration of the standard. The primer amplification efficiencies are shown in Table 4.

TABLE 4

| Primer amplification efficiency | | | | |
|---|---|---|---|---|
| Gene | Y-Intercept | Slope | $R^2$ | E (%) |
| pbrT | 53.59 | −4.1 | 0.9986 | 75.30 |
| chrA | 46.7 | −3.88 | 0.9997 | 80.90 |
| czcD | 47.58 | −3.88 | 0.9988 | 81.10 |

As obtained from the Table 4, the regression equation of pbrT fragment of Pb resistant gene is Y=−4.1X+53.59, with correlation coefficient $R^2$=0.9986; the regression equation of chrA fragment of Cr resistant gene is Y=−3.88X+46.7, with correlation coefficient $R^2$=0.9997; the regression equation of czcD fragment of Cd resistant gene is Y=−3.88X+47.58, with correlation coefficient $R^2$=0.9988; all three linear relationships are relatively good. X is log Co (gene copy number), and Y is Ct (i.e., the number of amplification cycles corresponding to the time when the fluorescence signal of the amplification product reaches the set fluorescence threshold).

Figure 9:
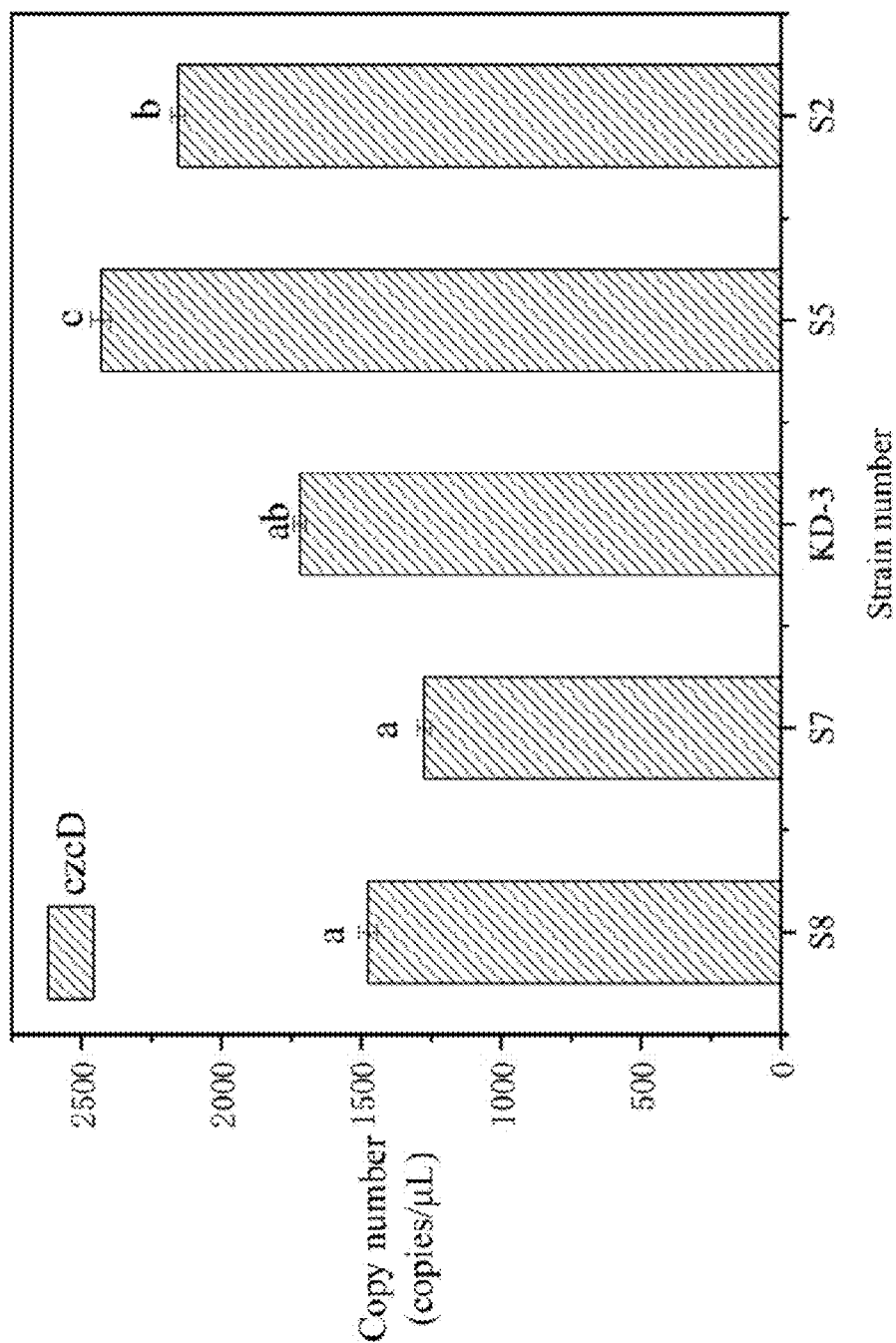
FIG. 9 shows the absolute quantitative expression levels of cadmium resistant genes in lactic acid bacteria.

5. The genomic DNA of five strains S8, S7, KD-3, S5 and S2 are extracted respectively, and the genomic DNA of the strains and the resistant gene standard are amplified by absolute quantitative fluorescence PCR at the same time, and the final copy number of the resistant genes of the genomic DNA of the five strains is obtained finally, with results as shown in FIG. 9. The expression levels of the three resistant genes in different strains are analyzed for significant differences using SPSS 16.0 (p<0.05 is considered significant and p<0.01 is considered highly significant).

It may be seen that, among them, the cadmium resistant gene fragment czcD is expressed in strain S5 at 2430.74±35.2 copies/μL, significantly higher than the other strains, and czcD is expressed in strain KD-3 at 1719.47±21.5 copies/μL, as shown in FIG. 9.

Figure 10:
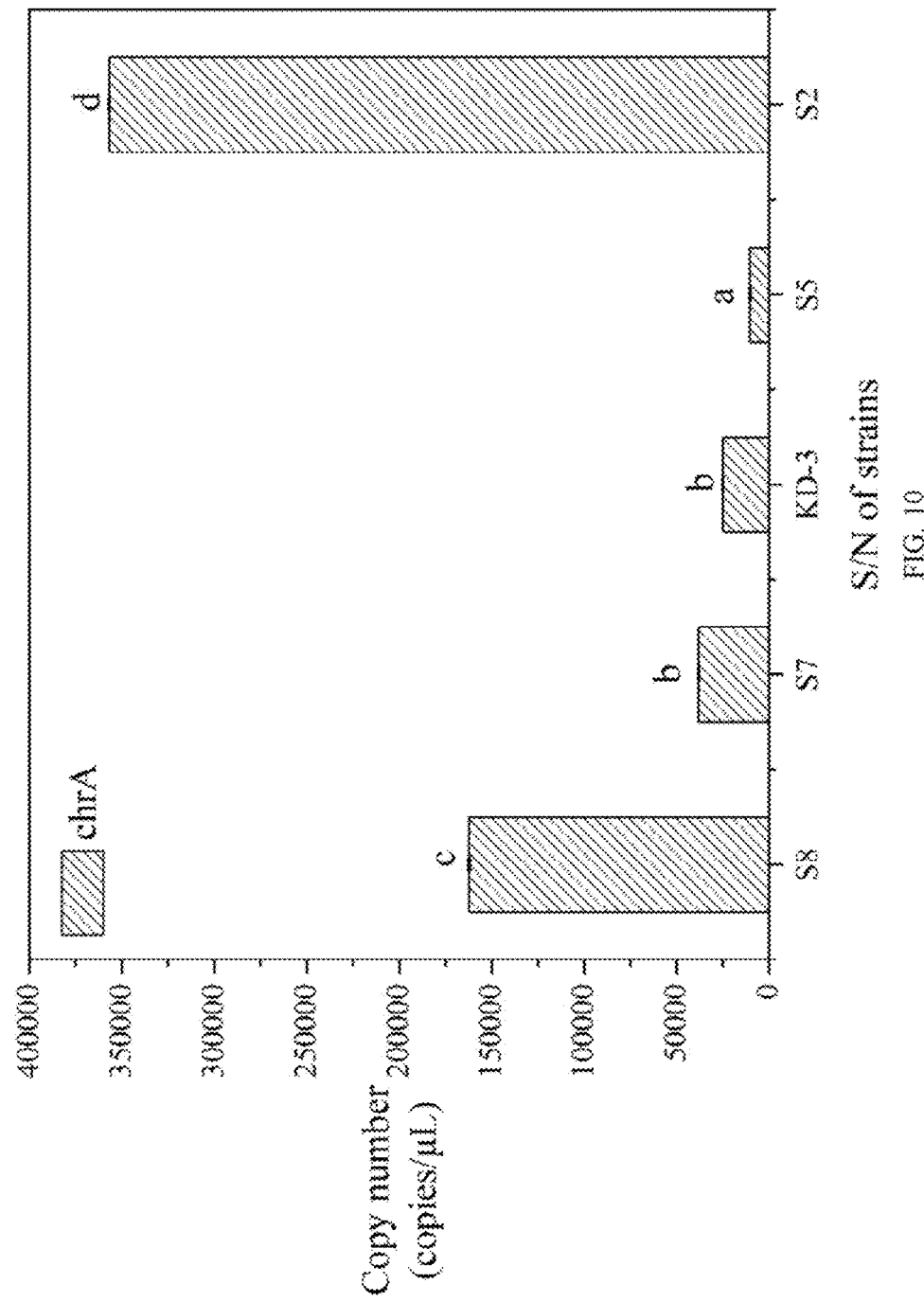
FIG. 10 shows the absolute quantitative expression levels of chromium resistant genes in lactic acid bacteria.

The expression levels of the chromium resistant gene fragment chrA in each strain are shown in FIG. 10, with 3.57×10$^5$ copies/μL in strain S2 and 24474.05±572.4 copies/μL of chrA in strain KD-3.

The lead resistant gene fragment pbrT is only detected in strain KD-3 with an expression of 1.26×10$^4$ copies/L, and this gene fragment is not detected in the rest of the strains.

In summary, KD-3, which simultaneously possesses a variety of well-characterized anti-$Cd^{2+}$, $Pb^{2+}$, $Cr^{6+}$ gene fragments, is used as a target strain for strain identification.

6. Identification of Strain KD-3

Figure 11:
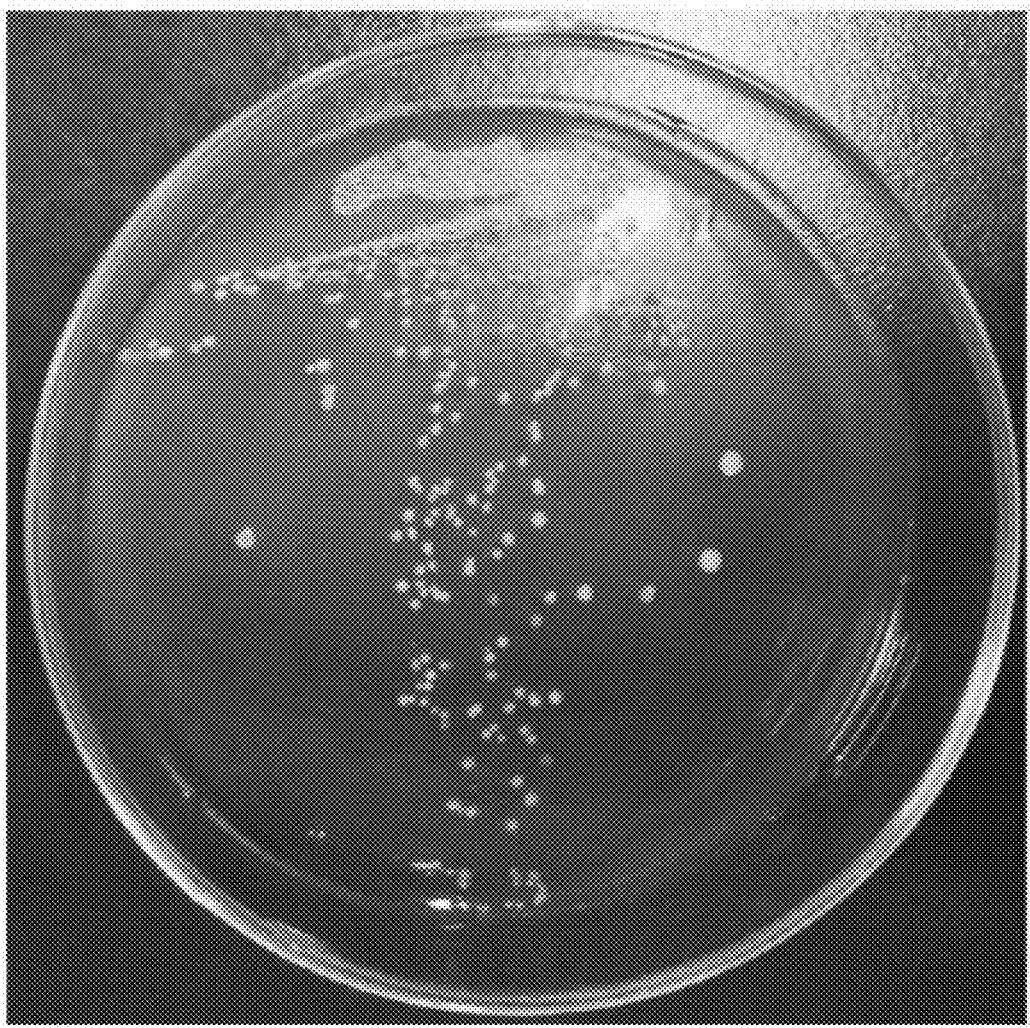
FIG. 11 shows the colony morphology of *Lactobacillus helveticus* KD-3.
Figure 12:
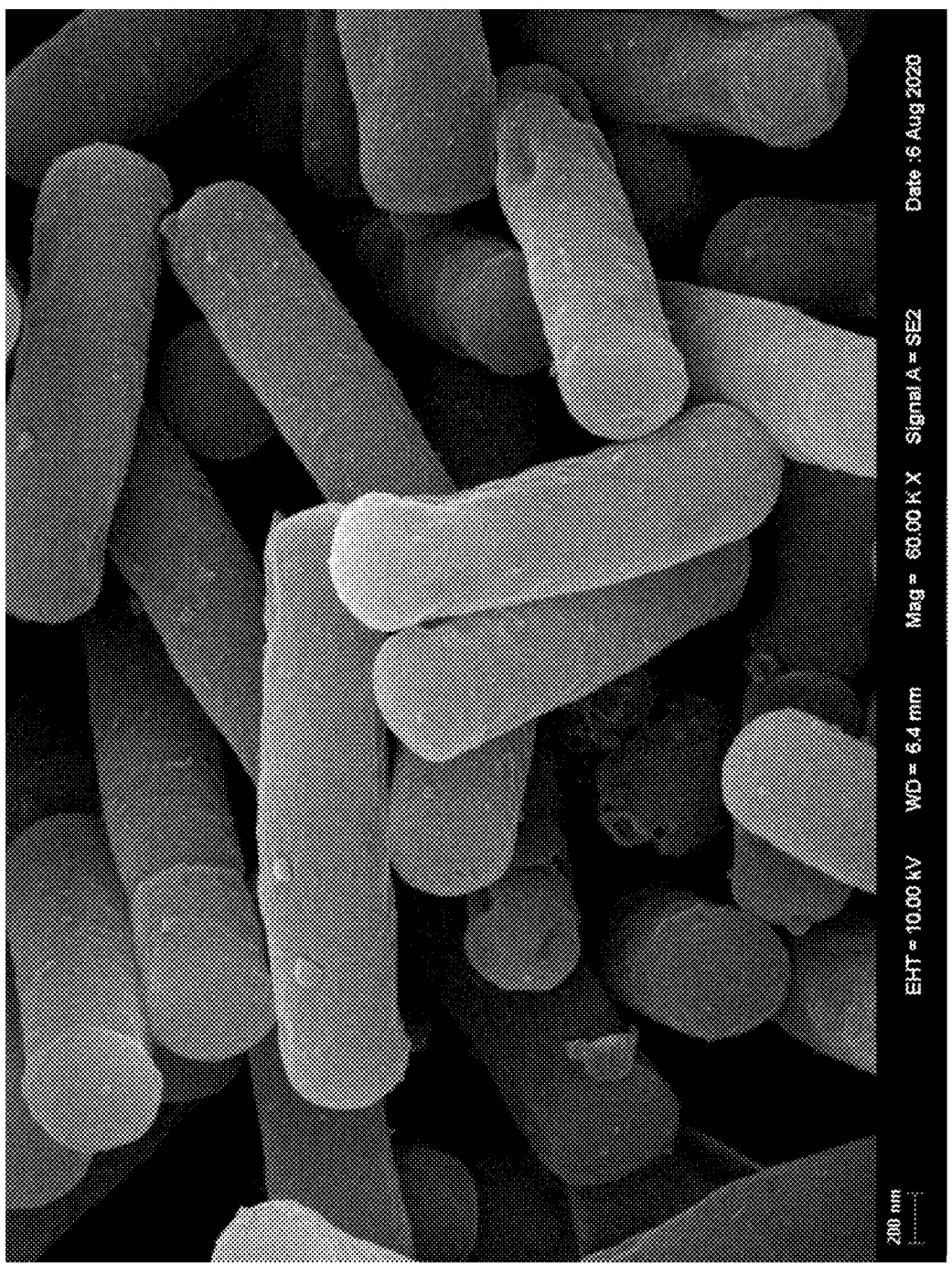
FIG. 12 shows the surface micromorphology of *Lactobacillus helveticus* KD-3 cells under scanning electron microscope.

The *Lactobacillus helveticus* KD-3 is cultured at 37° C. for 24 h and placed under microscope and scanning electron microscope to observe the colony characteristics, with results as shown in FIGS. 11 and 12; under the microscope, the cells are rod-shaped, and there is a phenomenon of aggregation of the cells under the microscope after toluidine blue staining; the colonies are milky-white with convex, and the appearance is relatively smooth, the cellular morphology is in line with the typical morphology characteristics of the lactic acid bacteria. Scanning electron microscopy results show that the surface of the cells is smooth and free of foreign matter, and the cells is rod-shaped and full.

The 16S rDNA gene fragment of strain KD-3 is extracted for strain identification, and the 16S rDNA gene sequence is shown in SEQ ID NO. 1. The sequence of the measured 16S rDNA gene fragment is compared and analyzed with the base sequences in the NCBI database, and the phylogenetic tree of the strain is constructed, as shown in FIG. 13.

Figure 13:
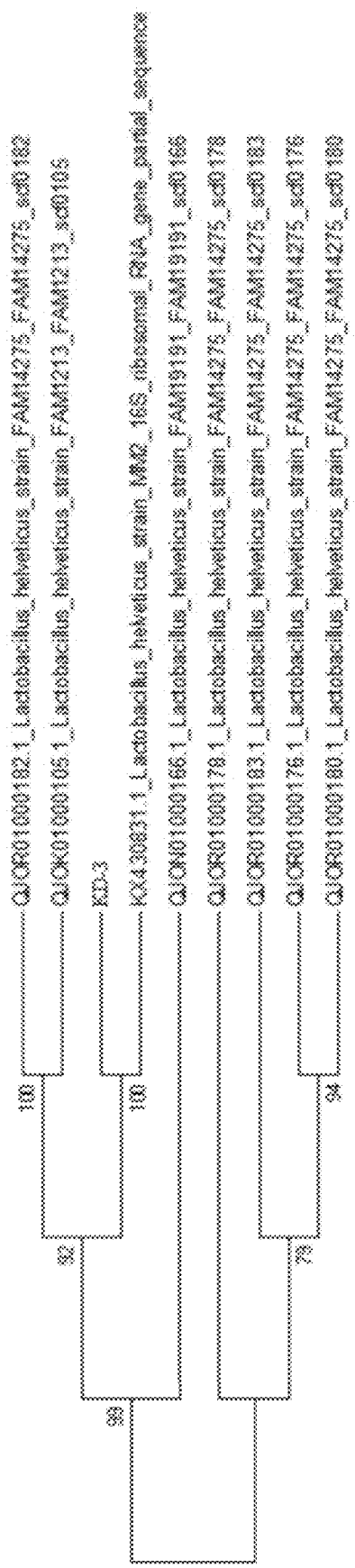
FIG. 13 shows the phylogenetic tree of *Lactobacillus helveticus* KD-3.
Figure 14:
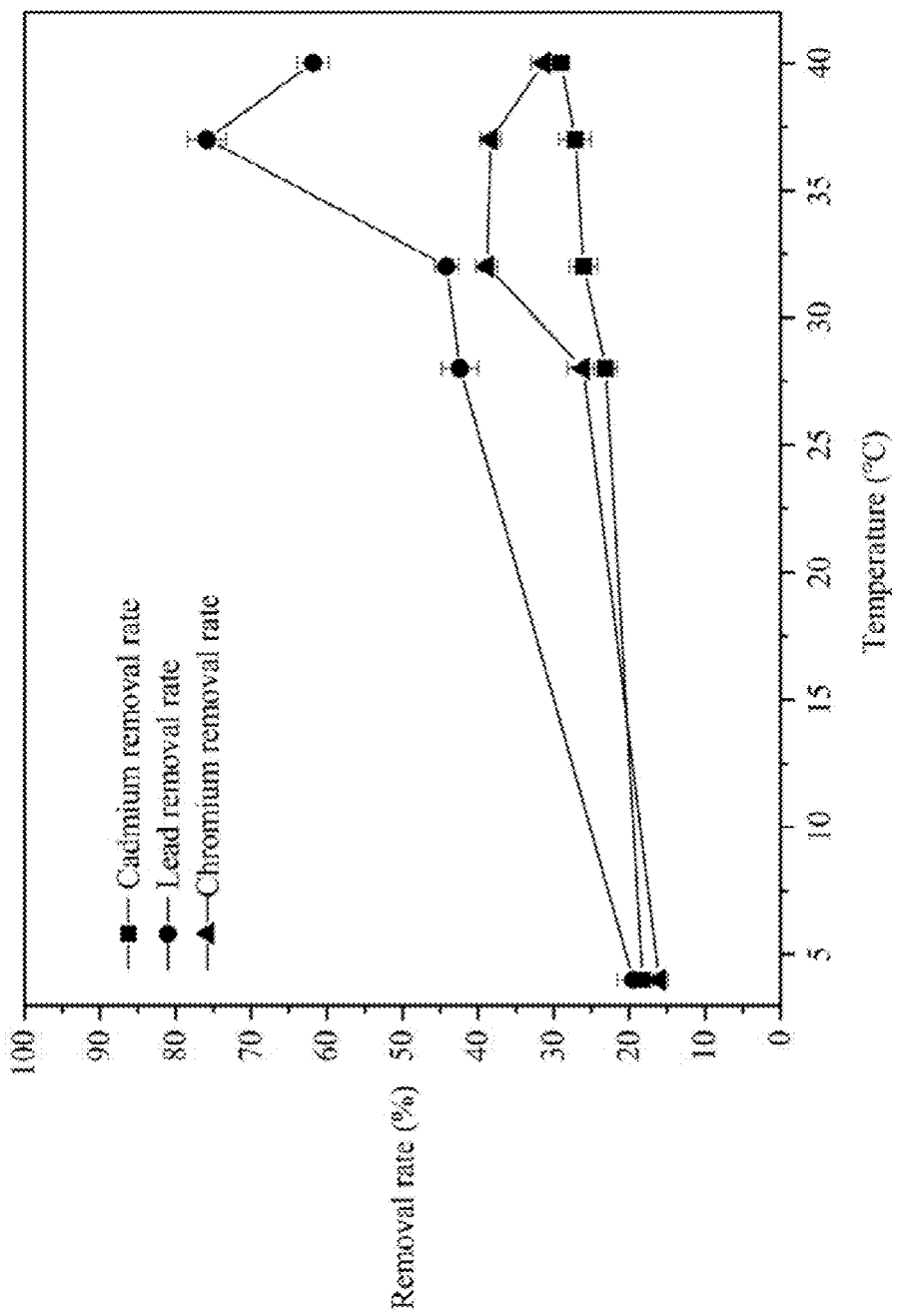
FIG. 14 shows the effect of temperature on the adsorption of heavy metals by *Lactobacillus helveticus* KD-3.
Figure 15:
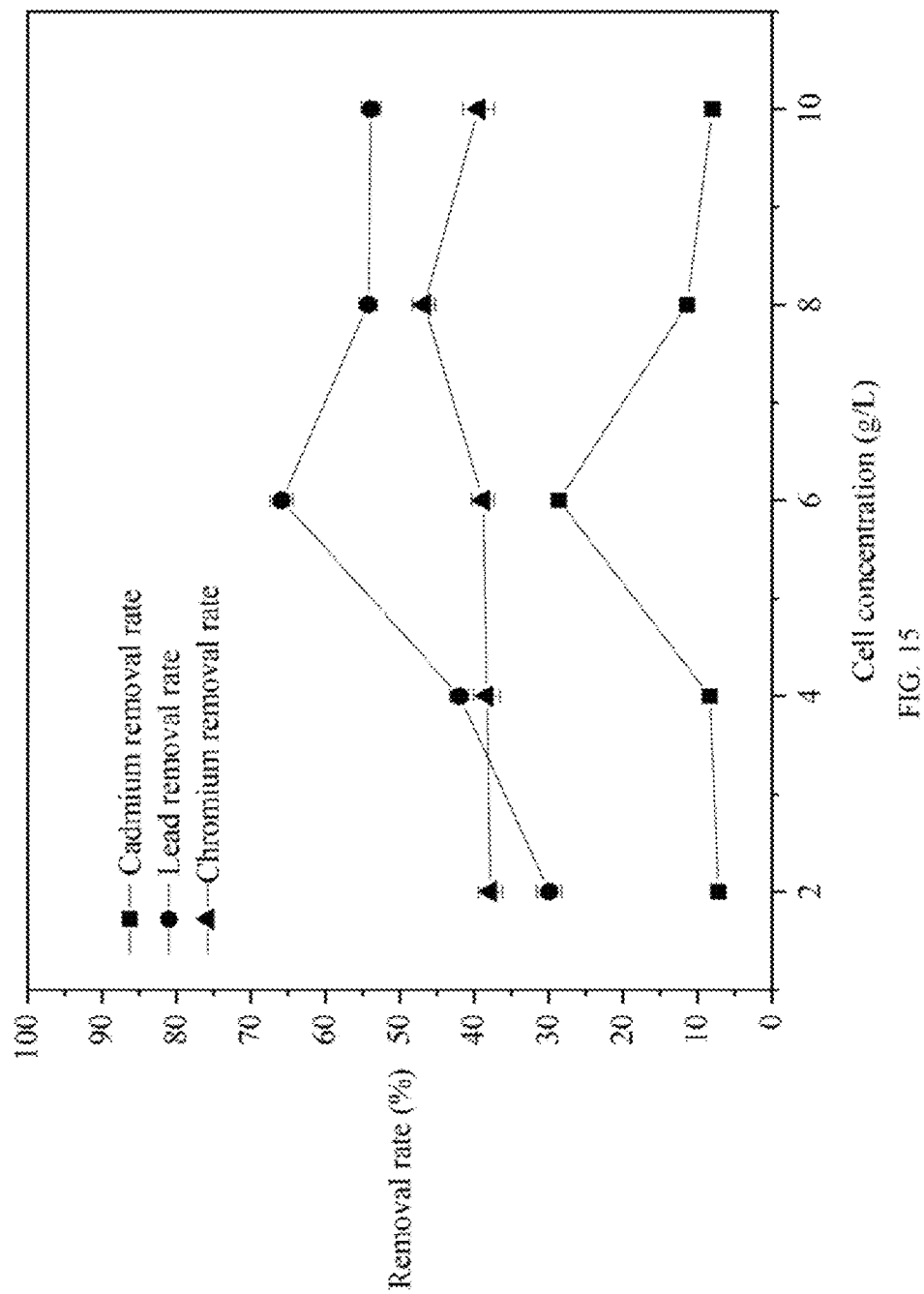
FIG. 15 shows the effect of different cells additions on the adsorption of heavy metals by *Lactobacillus helveticus* KD-3.
Figure 16:
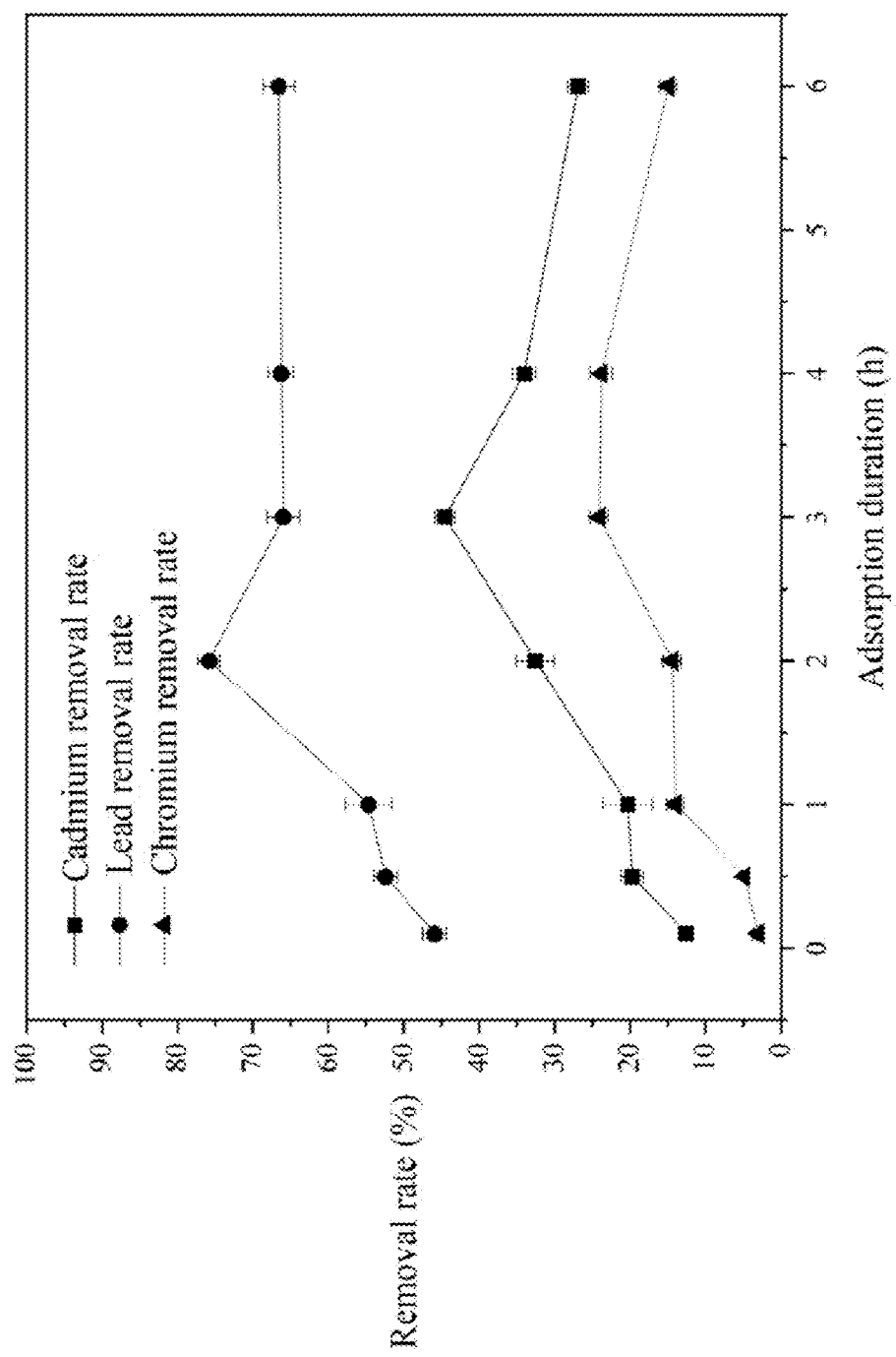
FIG. 16 shows the effect of different adsorption duration on the adsorption of heavy metals by *Lactobacillus helveticus* KD-3.
Figure 17:
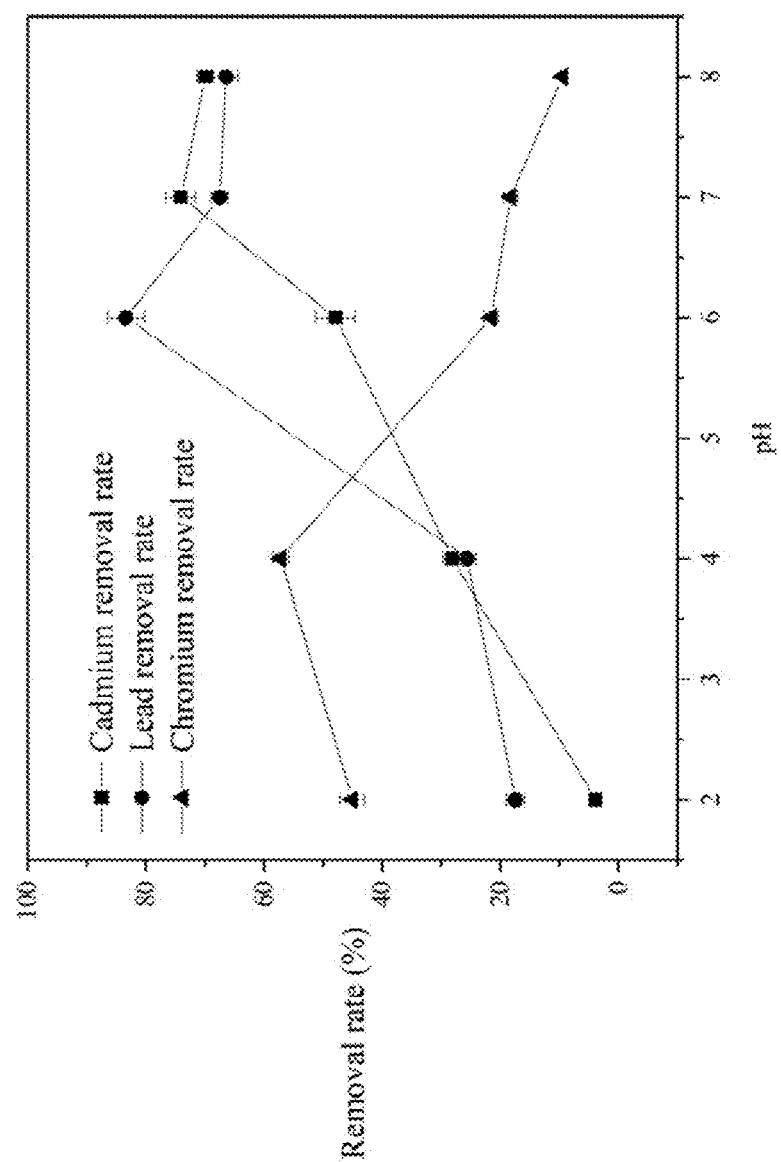
FIG. 17 shows the effect of different starting pH values on the adsorption of heavy metals by *Lactobacillus helveticus* KD-3.

The FIG. 13 shows that the strain KD-3 is *Lactobacillus helveticus*, i.e., *Lactobacillus helveticus* KD-3.

Embodiment 3

The effects of optimal growth temperature, pH value, inoculum amount and NaCl concentration on the growth of *Lactobacillus helveticus* KD-3 are determined using MRS broth liquid medium. The OD (at 600 nm) values of *Lactobacillus helveticus* KD-3 strain are determined to indicate the real-time growth of the strain by changing the pH, inoculum amount, culture temperature and culture duration of the culture medium and under different osmotic pressure conditions by the controlled variable method.

It is measured that the optimal culture temperature of *Lactobacillus helveticus* KD-3 is 37-40° C., and the optimal culture temperature is 37° C.; the optimal pH range for the growth of *Lactobacillus helveticus* is 5-8, and the optimal pH is 7; the inoculum amount is 2-5% of the volume of the medium, and the inoculum amount 3% of the volume of the medium achieves the best culture effect; the culture duration is 24-48 h, and the optimal culture duration is 24 h; the concentration of NaCl has a relatively great effect on the growth of *Lactobacillus helveticus* KD-3; with the increase of NaCl concentration, when the NaCl concentration is of 1%-2% in the medium, the growth of the strain is not significantly different, and the strain is capable of tolerating the NaCl solution with a mass concentration of 2%.

1. Analysis of the Effect of Adsorption Conditions on the Adsorption of Lead, Cadmium and Chromium Ions by *Lactobacillus helveticus* KD-3

(1) Preparation of *Lactobacillus helveticus* KD-3 Cells

The cells are used for adsorption in order to avoid the influence of the protective agent on metal adsorption. The isolated and purified *Lactobacillus helveticus* KD-3 is inoculated in MRS broth liquid medium and incubated in a constant temperature incubator at 37° C. for 24 h, then centrifuged at 8000 rpm for 15 min to collect the cells, which are washed with sterile saline for two times and then centrifuged again to obtain the cells.

(2) The above cells are inoculated to the lead-cadmium mixed solution (100 mg/L) and chromium solution (100 mg/L) for adsorption of heavy metals, and the basic adsorption conditions are set with the adsorption duration of 3 h, the addition of the cells to the volume of solution containing cadmium and leads of 5%, pH of 6, and the temperature of 37° C. Different temperatures (4° C., 28° C., 32° C., 37° C., 40° C.), addition of the cells (i.e., the ratio of the cells to the mass volume of the solution containing the heavy metals cadmium and lead) of 2%, 4%, 6%, 8%, and 10% of the volumes of the solution containing cadmium and lead and of the volume of the solution containing chromium alone respectively, the adsorption duration (0.1 h, 0.5 h, 1 h, 2 h, 3 h, 6 h), and the initial pH values (2, 4, 6, 7, 8) are set for adsorption. Among them, the adjustment of initial pH is realized by adding dilute nitric acid or sodium hydroxide solution. Three parallel experiments are set for each treatment during the experiment.

(3) The metal ion concentration in the resulting supernatant is determined using inductively coupled plasma mass spectrometry (ICP-MS) after adsorption is completed, and the metal removal rate is calculated compared to the control group, which is a mixed solution of lead and cadmium without inoculation of *Lactobacillus helveticus* KD-3 under the same culture conditions or a chromium solution without inoculation of *Lactobacillus helveticus* KD-3 under the same culture conditions. The formula for calculating the removal rate is the same as in Embodiment 1, and the results are shown in FIGS. 14 to 17 and Tables 5 to 8.

Cadmium removal rate reaches a maximum of 29.08±1.13% at 40° C.; lead ion removal rate reaches a maximum of 75.88±2.54% at 37° C.; and chromium ion removal rate reaches a maximum of 38.85±1.45% at 32° C.

With the increase of bacterial addition, both lead and cadmium ion removal rates reach the maximum when *Lactobacillus helveticus* KD-3 cells is inoculated to the mixed solution of lead and cadmium with the volume ratio of 6%, the maximum value of the lead removal rate, cadmium removal rate is 65.87±1.55% and 28.64±0.48%, respectively; the adsorption of chromium ions increases slowly with the addition of the cells and reaches a maximum value of 46.74±1.52% by the volume ratio of *Lactobacillus helveticus* KD-3 cells inoculated to the chromium solution of 8‰.

With adsorption at 3 h, cadmium removal rate reaches a maximum value of 44.53±1.31%; lead ion adsorption reaches 75.81±1.42% at 2 h and then decreases and then gradually levels off; chromium removal rate reaches a maximum value of 24.08±1.2% after 3 h of adsorption and then gradually decreases.

Cadmium removal rate reaches a maximum of 54.1±2.54% at pH 7; lead ion removal rate reaches a maximum of 83.37±3.1% at pH 6; and *Lactobacillus helveticus* KD-3 has the highest removal rate of chromium ions of 57.16±1.4% at pH 4; indicating that an acidic environment is more conducive to chromium ion adsorption.

TABLE 5

Cadmium removal rate and lead removal rate by *Lactobacillus helveticus* KD-3 at different adsorption temperatures

| Adsorption temperature (° C.) | Cadmium removal rate (%) | Lead removal rate (%) | Chromium removal (%) |
| --- | --- | --- | --- |
| 4 | 18.3 ± 1.42 | 19.47 ± 2.12 | 16.09 ± 1.21 |
| 28 | 23.17 ± 1.56 | 42.4 ± 2.41 | 26.1 ± 2.1 |
| 32 | 26.06 ± 1.89 | 44.18 ± 1.56 | 38.85 ± 1.45 |
| 37 | 27.19 ± 2.1 | 75.88 ± 2.54 | 38.34 ± 1.31 |
| 40 | 29.08 ± 1.13 | 61.84 ± 2.13 | 31.29 ± 1.67 |

TABLE 6

Cadmium removal rate and lead removal rate by *Lactobacillus helveticus* KD-3 at different bacterial additions

| Addition of cells | Cadmium removal rate (%) | Lead removal rate (%) | Chromium removal rate (%) |
| --- | --- | --- | --- |
| 2‰ | 7.2 ± 0.31 | 29.92 ± 1.68 | 37.82 ± 1.63 |
| 4‰ | 8.35 ± 0.22 | 42 ± 1.22 | 38.31 ± 1.76 |
| 6‰ | 28.64 ± 0.48 | 65.87 ± 1.55 | 38.79 ± 1.52 |
| 8‰ | 11.37 ± 0.51 | 54.26 ± 1.25 | 46.74 ± 1.52 |
| 10‰ | 8.01 ± 0.87 | 53.88 ± 1.31 | 39.39 ± 2.13 |

TABLE 7

Cadmium removal rate and lead removal rate by *Lactobacillus helveticus* KD-3 at different adsorption times

| Adsorption duration (h) | Cadmium removal rate (%) | Lead removal rate (%) | Chromium removal rate (%) |
| --- | --- | --- | --- |
| 0.1 | 12.59 ± 0.21 | 45.92 ± 1.53 | 3.02 ± 0.72 |
| 0.5 | 19.73 ± 1.53 | 52.39 ± 1.52 | 4.85 ± 0.4 |
| 1 | 20.32 ± 3.31 | 54.63 ± 3.1 | 14.04 ± 1.1 |
| 2 | 32.55 ± 2.54 | 75.81 ± 1.42 | 14.44 ± 1.21 |
| 3 | 44.53 ± 1.31 | 65.94 ± 2.12 | 24.08 ± 1.2 |
| 4 | 34.03 ± 1.53 | 66.22 ± 1.67 | 23.82 ± 1.42 |
| 6 | 26.88 ± 1.42 | 66.57 ± 2.1 | 14.93 ± 1.1 |

TABLE 8

Cadmium removal rate and lead removal rate by *Lactobacillus helveticus* KD-3 at different pH values

| pH | Cadmium removal rate (%) | Lead removal rate (%) | Chromium removal rate (%) |
| --- | --- | --- | --- |
| 2 | 3.9 ± 0.21 | 17.48 ± 1.53 | 45.08 ± 2.1 |
| 4 | 28.16 ± 1.53 | 25.63 ± 1.52 | 57.16 ± 1.4 |
| 6 | 37.9 ± 3.31 | 83.37 ± 3.1 | 21.58 ± 1.1 |
| 7 | 54.1 ± 2.54 | 67.49 ± 1.42 | 18.29 ± 1.21 |
| 8 | 49.94 ± 1.31 | 66.46 ± 2.12 | 9.51 ± 0.12 |

2. Adsorption Conditions Optimization of Lead and Cadmium Ions by *Lactobacillus helveticus* KD-3

The preparation method of the *Lactobacillus helveticus* KD-3 cells is same as in step 1.

In order to further optimize the adsorption process under the mixed environment of lead and cadmium, a solution containing both heavy metals cadmium and lead is utilized, and the adsorption duration (A), temperature (B), initial pH value (C), and addition amount of the cells (D) (i.e., the ratio of cells to the mass-volume ratio of the solution containing the heavy metals cadmium and lead) are selected to further optimize the adsorption conditions, and the design of the experiment and the results are as shown in Table 9, and the formula for the removal rate is the same as that of Embodiment 1.

TABLE 9

Experimental results of adsorption of heavy lead and cadmium ions by *Lactobacillus helveticus* KD-3

| Serial number | A | B | C | D | Cadmium removal rate (%) | Lead removal rate (%) |
|---|---|---|---|---|---|---|
| 1 | 2.50 | 45 | 7.50 | 6.00 | 65.67 | 73.14 |
| 2 | 2.50 | 40 | 7.50 | 5.00 | 45.30 | 86.60 |
| 3 | 2.50 | 45 | 6.50 | 5.00 | 38.48 | 81.33 |
| 4 | 3.50 | 40 | 6.50 | 7.00 | 37.07 | 89.81 |
| 5 | 1.50 | 40 | 6.50 | 5.00 | 36.50 | 97.08 |
| 6 | 2.50 | 35 | 7.50 | 6.00 | 39.82 | 74.50 |
| 7 | 3.50 | 40 | 7.50 | 6.00 | 65.37 | 78.27 |
| 8 | 2.50 | 40 | 7.50 | 7.00 | 51.73 | 82.56 |
| 9 | 2.50 | 40 | 6.50 | 6.00 | 39.07 | 75.91 |
| 10 | 2.50 | 45 | 6.50 | 7.00 | 50.05 | 72.45 |
| 11 | 1.50 | 45 | 7.50 | 5.25 | 64.56 | 87.93 |
| 12 | 1.50 | 45 | 6.50 | 6.00 | 59.28 | 78.38 |
| 13 | 2.50 | 40 | 6.50 | 6.00 | 38.09 | 94.17 |
| 14 | 3.50 | 45 | 6.50 | 6.00 | 49.76 | 70.14 |
| 15 | 1.50 | 40 | 7.50 | 6.00 | 53.17 | 83.73 |
| 16 | 1.50 | 40 | 6.50 | 7.00 | 45.99 | 92.53 |

As can be seen from Table 9, under the conditions that the amount of bacterium added is 5-7% of the volume of the solution containing heavy metals cadmium and lead, pH is 6.5-7.5, temperature is 35-45° C. and adsorption duration is 1.5-3.5 h, the removal rate of cadmium in the cadmium-lead mixed solution is 36.50%-65.67%, and the removal rate of lead is 72.45%-94.17%, and preferably when the amount of cells added is 5.25%, pH is 7.50, temperature is 45° C., and adsorption duration is 1.5 h, the removal rate of cadmium in the cadmium-lead mixed solution is 364.56%, the adsorption rate per unit of cells is 127 mg/g, and removal rate of lead is 87.93%, and the adsorption rate per unit of cells is 378 mg/g.

The heavy metal removal performance of *Lactobacillus helveticus* KD-3 is compared with the strains in the prior art and the results are shown in Table 10.

The removal of most single metals is better than that of multiple metals, and the adsorption studies of composite heavy metals are shown in Table 5, *Lactobacillus helveticus* KD-3 has a higher adsorption capacity than most bacteria for lead, cadmium, and chromium single heavy metals in the fermentation environment; and in the adsorption of the compound heavy metals lead and cadmium in the in vitro solution, the adsorption capacity of lead and cadmium is better than that of most of the reported strains. *Lactobacillus helveticus* KD-3 has a higher adsorption capacity than most bacteria for lead, cadmium, and chromium single heavy metals in a fermentation environment; and in vitro solution adsorption of the composite heavy metal lead-cadmium is better than most reported strains.

Reference [1] Masood F, Malik A. Single and Multi-Component Adsorption of Metal Ions by *Acinetobacter* sp. FM4[J]. Separation Science & Technology, 2015, 50(6):892-900.

Reference [2] Ziagova M, Dimitriadis G, Aslanidou D, et al. Comparative study of the effect of Cd(II) and Cr(VI) biosorption on *Staphylococcus* xylosus and *Pseudomonas* sp. in single and binary mixtures[J]. Bioresource Technology, 2007, 98(15):2859-2865.

Reference [3] Meenakshi S, Megha V, J. P. N. Rai. Biosorption of heavy metals from single and multimetal solutions by free and immobilized cells of *Bacillus megaterium*[J]. International Journal of Advanced Research (IJAR), 2014, 2(6): 923-934.

Reference [4] Parungao M M, Tacata P S, Ray C, et al. Biosorption of copper, cadmium and lead by copper-resistant bacteria isolated from Mogpog River, Marinduque[J]. Philippine Journal of Science, 2007, 136(2): 155-165.

Reference [5] Wang T, Sun H. Biosorption of heavy metals from aqueous solution by UV-mutant *Bacillus subtilis*[J]. Environmental Science & Pollution Research International, 2013, 20(10):7450-7463.

Embodiment 4 Development of *Lactobacillus helveticus* KD-3 Goat Milk Powder and Evaluation of In Vitro Removal of Heavy Metals 1. Comparison of the Adsorption of Lead and Cadmium by *Lactobacillus helveticus* KD-3 in Different States In order to promote the application of *Lactobacillus helveticus* KD-3 in fermented foods, it is designed to com-

TABLE 10

Results of heavy metal removal performance of *Lactobacillus helveticus* KD-3 compared to strains in the prior art

| Compound heavy metals | Bacterial species | Single-metal adsorption properties | Compound metal adsorption capacity | Bibliography |
|---|---|---|---|---|
| Cr, Cu, Ni | *Acenetobacter* sp. FM4 | 100 mg/g (Cr) | 61 mg/g (Cr) | [1] |
| Cr, Cd | *Pseudomonas* sp. | 278 mg/g (Cd) 95 mg/g (Cr) | 150 mg/g (Cd) 25 mg/g (Cr) | [2] |
| Cr, Cd | *Staphylococcus xylosus* | 250 mg/g (Cd) 143 mg/g (Cr) | 130 mg/g (Cd) 12.5 mg/g (Cr) | |
| Pb, Cr, Cd | *Bacillus megaterium* | 60 mg/g (Pb) 40.32 mg/g (Cd) 18.92 mg/g (Cr) | 43.48 mg/g (Pb) 25.67 mg/g (Cd) 13.56 mg/g (Cr) | [3] |
| Cu, Cd, Pb | *Stenotrophomonas maltophilia* | 24% (Cd) 42.75% (Pb) | 8% (Cd), 35% (Pb) | [4] |
| Cd, Hg, Pb | *Bacillus subtilis* | 208.08 mg/g (Cd) 400.75 mg/g (Pb) | 58.93 mg/g (Cd); 288.95 mg/g (Pb) | [5] |
| Pb, Cr, Cd | *Lactobacillus helveticus* KD-3 | 142 mg/g (Pb) 159 mg/g (Cd) 207 mg/g (Cr) | 378 mg/g (Pb) 127 mg/g (Cd) | Present application | pare the effects of different states of the cells on the removal of lead and cadmium by the strain.

Treatment 1: fresh *Lactobacillus helveticus* KD-3 is inoculated in MRS broth liquid medium at 5% by volume, and the viable cells are obtained by freezing and centrifugation at 4° C. and 8000 rpm for 10 min after 24 h of culture;

Treatment 2: the viable cells after taken out are sterilized at 121° C. for 20 min in an autoclave to obtain dead organisms;

Treatment 3: protective agents (glucose, D-galactose, ascorbic acid) are added to the viable cells to obtain the cells incorporating the protective agents. The amounts of glucose, D-galactose and ascorbic acid added are 2%, 2.5% and 0.1% of the weight of the cells, respectively.

Treatment 1-Treatment 3 are added to the aqueous solution containing lead and cadmium ions of 10 mg/L at a final concentration of 0.5 g/L, followed by oscillatory adsorption at 37° C. for 3 h, and the obtained material is centrifuged at 8000 rpm for 10 min, then the content of lead and cadmium in the supernatant is determined by ICP emission spectrometry, and the adsorption capacity of KD-3 in different states is compared.

Figure 18:
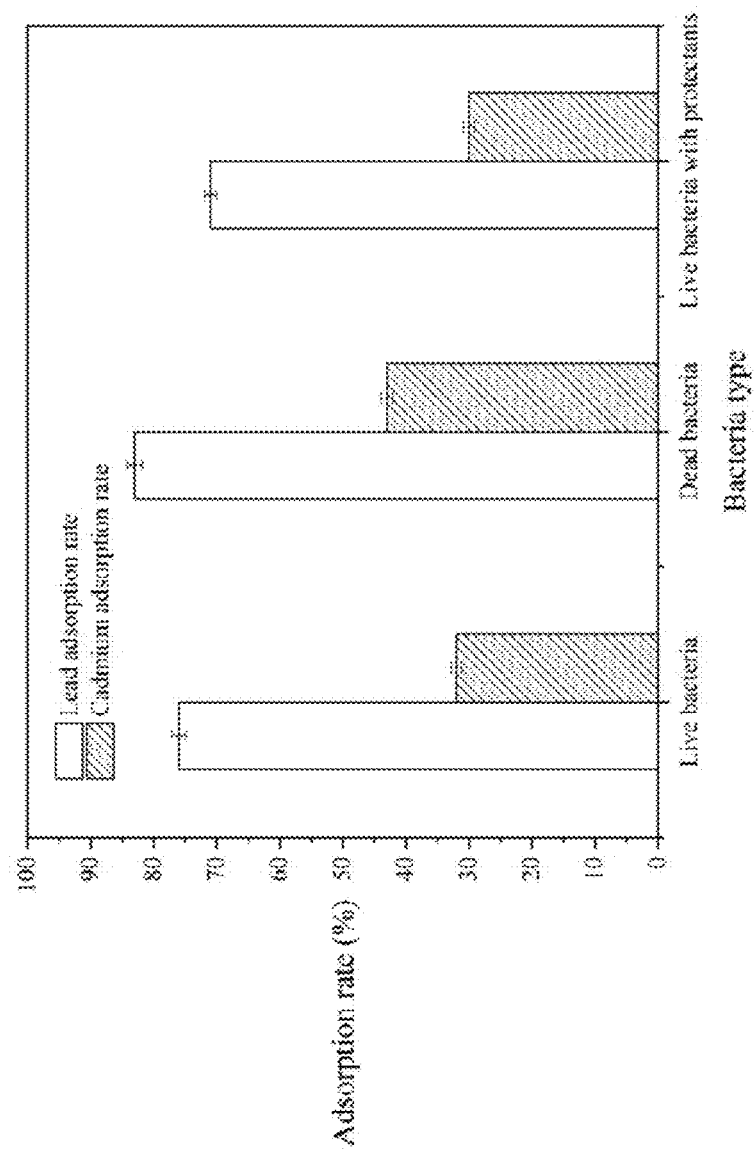
FIG. 18 shows the effect of different states of *Lactobacillus helveticus* KD-3 on adsorption of lead and cadmium.

According to the results as shown in FIG. 18, it may be seen that the lead adsorption rate of the dead bacteria is 83±1.2% and cadmium adsorption rate is 43±0.92%; the lead adsorption rate of the viable bacteria is 76±1.1% and cadmium adsorption rate is 32±0.78%; the lead adsorption rate of the viable bacteria added with protective agent is 71±0.97% and the cadmium adsorption rate is 30±0.89%, suggesting that the adsorption of the three states of *Lactobacillus chrysogenum* KD-3 on lead and cadmium has no significant difference (p>0.05); while the removal rate of lead and cadmium by the dead bacteria is slightly increased, which may be due to the destruction of the surface of the bacteria by high temperature and high pressure, resulting in the exposure of more adsorption sites, which in turn facilitates the surface adsorption. The reduction in removal rate after adding the protective agent may be caused by the lower amount of actual bacteria due to the addition of the protective agent.

2. Removal of Lead and Cadmium from Simulated Gastrointestinal Fluid by *Lactobacillus helveticus* KD-3 Goat Milk Powder The *Lactobacillus helveticus* KD-3 is inoculated into 500 mL MRS broth liquid medium according to the inoculum amount of 3% by volume ratio, and then cultured at 40° C. for 24 h, then centrifuged at 8000 rpm for 10 min, and the resulting precipitate is washed with sterile saline for three times, and the supernatant is discarded, and then the cells are collected, the cells is then added with the protective agent and mixed well; the cells powder is prepared by vacuum freeze-drying the *Lactobacillus helveticus* KD-3, and the parameters of vacuum freeze-drying are placing into the −35° C. environment for 5 h, and then freeze-drying at −55° C. under vacuum degrees of 5 pa for 24 h; 0.1 g of the cells powder after drying is evenly dry-mixed with 100 g of goat milk powder, and the number of viable bacteria is determined by plate counting method, so as to develop functional goat milk powder for removing heavy metals. The viable bacterial count of *Lactobacillus helveticus* KD-3 powder is $3.25 \times 10^{11}$ CFU/g. The viable bacterial count of *Lactobacillus helveticus* KD-3 in goat milk powder is $3.25 \times 10^7$ CFU/g.

The prepared goat functional goat milk powder for removing heavy metals is diluted with distilled water at a mass concentration of 12.5%, and 10 mL of the diluted solution is added to 20 mL of simulated gastric fluid to be digested for 2 h, where the lead and cadmium concentration in the simulated gastric fluid is 10 mg/L, then the supernatant and the bacterial precipitation are obtained by centrifugation, and the lead and cadmium residues in the supernatant are measured; after that, 20 mL of the artificial intestinal fluid is added to the bacterial precipitation to continue the adsorption for 3 h, where the concentration of lead and cadmium in the artificial intestinal fluid is 10 mg/L, after which centrifugation is performed to obtain the residual amount of lead and cadmium in the supernatant.

Goat milk powder without *Lactobacillus helveticus* KD-3 powder is added to the gastrointestinal fluid treatment as a control group to determine the heavy metal removal of *Lactobacillus helveticus* KD-3 in the simulated gastrointestinal fluid.

Figure 19:
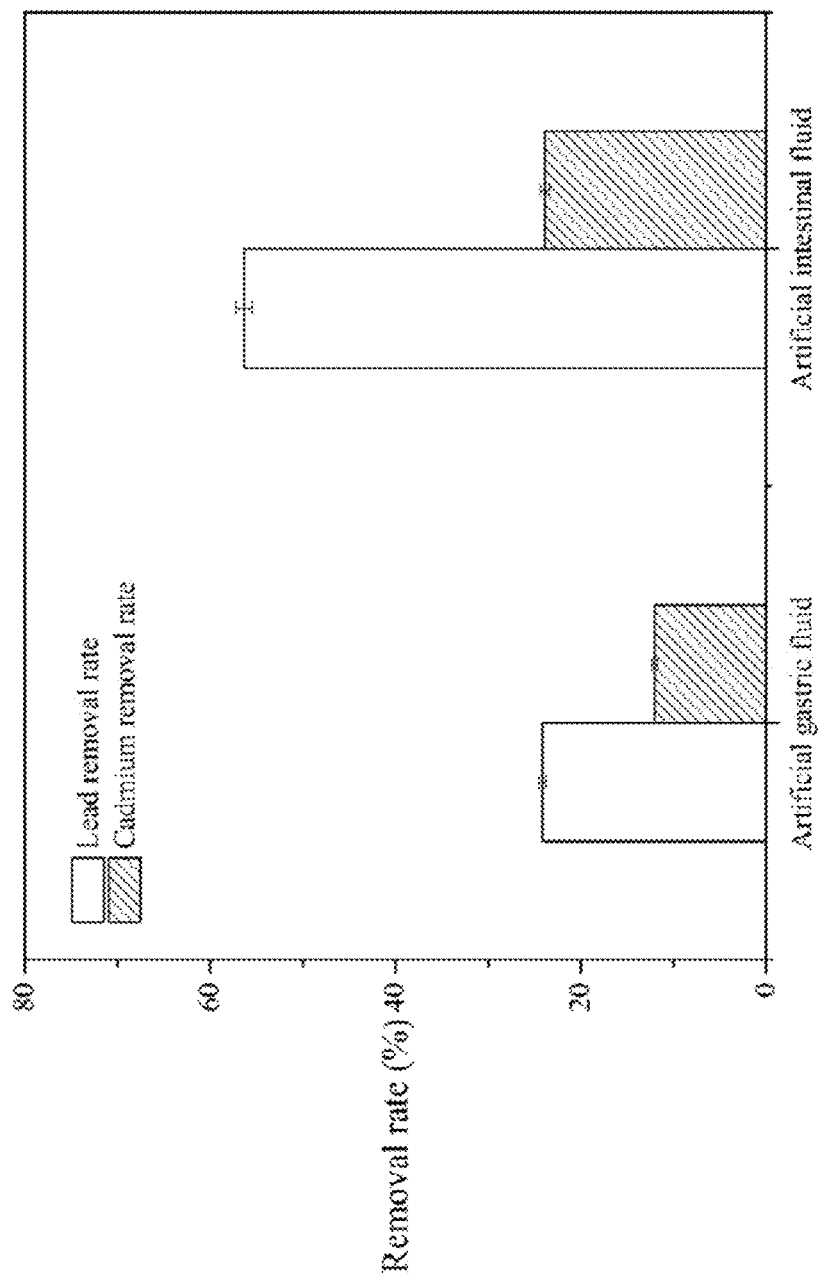
FIG. 19 shows the clearance of lead and cadmium from simulated gastrointestinal fluid by *Lactobacillus helveticus* KD-3 goat milk powder.

As may be seen in FIG. 19, the removal rate of lead and cadmium is higher in the artificial intestinal fluid environment, reaching 56.31±1.72% and 23.87±1.97%, respectively. The removal rate of lead and cadmium is lower in artificial gastric fluid, being 24.12±1.34% and 12.02±0.98%, respectively, which may be due to the fact that the low acidic environment in the gastric fluid affects the adsorption performance of the strain, and the pH environment in the intestinal fluid is closer to the optimal adsorption environment, thus favoring the removal of heavy metals, with a significant increase in adsorption rate over gastric fluid ($p < 0.05$).

For liquid foods or solution systems that do not require fermentation, inactivated *Lactobacillus helveticus* KD-3 may be added directly to remove heavy metals from the food, and after adsorption, it may be separated out by centrifugation and filtration, etc. Alternatively, the *Lactobacillus helveticus* KD-3 cells powder may be added directly to the fermented food to alleviate the effects of heavy metal accumulation.

In summary, the adsorption capacity of *Lactobacillus helveticus* KD-3 for lead, cadmium and chromium single heavy metals in fermentation environment is higher than that of most of the bacteria; and in the in vitro solution adsorption of the compound heavy metals of lead and cadmium, the adsorption capacity for lead and cadmium is better than that of most of the reported strains. *Lactobacillus helveticus* KD-3 of the present disclosure is tolerant to single and compound heavy metals (cadmium, chromium and lead), and at the same time has a high removal efficiency for single and compound heavy metals (cadmium, chromium and lead). *Lactobacillus helveticus* KD-3 of the present disclosure may be used to prepare lyophilized bacterial powder, which is utilized to develop *Lactobacillus helveticus* KD-3 goat milk powder, and both the cells powder and the goat milk powder thereof are effective in removing heavy metals. By adding the prepared lyophilized bacterial powder of *Lactobacillus helveticus* KD-3 to goat milk powder to develop a probiotic goat milk powder with a viable bacterial count of $3.25 \times 10^7$ CFU/g, which is then applied to simulated gastrointestinal fluids for the removal of lead and cadmium ions, and a good removal effect is achieved.

Although the above embodiments make an exhaustive description of the present disclosure, it is only a part of the embodiments of the present disclosure, not all of the embodiments, and one may obtain other embodiments according to the present embodiments without creative premise, and these embodiments all belong to the scope of protection of the present disclosure.

What is claimed is:

1. A functional probiotic goat milk powder for removing heavy metals, wherein the functional probiotic goat milk powder comprises a lyophilized powder of viable cells of the *Lactobacillus helveticus* KD-3 strain and protective agents, wherein the protective agents comprise glucose, D-galactose, and ascorbic acid in amounts of 2%, 2.5%, and 0.1% respectively of the weight of the cells of the *Lactobacillus helveticus* KD-3 strain.

2. The functional probiotic goat milk powder according to claim 1, wherein an effective viable bacterial count of the *Lactobacillus helveticus* KD-3 strain in the functional probiotic goat milk powder is $\geq 3.0 \times 10^7$ CFU/g.

* * * * *